United States Patent [19]
Williamson, IV et al.

[11] Patent Number: 5,716,370
[45] Date of Patent: Feb. 10, 1998

[54] MEANS FOR REPLACING A HEART VALVE IN A MINIMALLY INVASIVE MANNER

[76] Inventors: Warren Williamson, IV, 101 Southbend Ct., Loveland, Ohio 45140; Paul A. Spense, 5818 Orion Rd., Louisville, Ky. 40222; George T. Christakis, 6 Playter Blvd., Toronto, Ontario, Canada, M4K 4V7

[21] Appl. No.: 606,343

[22] Filed: Feb. 23, 1996

[51] Int. Cl.⁶ .................................... A61B 17/08
[52] U.S. Cl. .................. 606/153; 606/151; 606/155; 623/2
[58] Field of Search .................. 623/2; 606/151, 606/153, 155, 156

[56] References Cited

U.S. PATENT DOCUMENTS

| | | |
|---|---|---|
| 3,491,376 | 1/1970 | Shiley . |
| 3,657,744 | 4/1972 | Ersek ........................ 606/153 |
| 3,727,240 | 4/1973 | Child . |
| 3,781,969 | 1/1974 | Anderson . |
| 4,506,394 | 3/1985 | Bedard . |
| 4,617,932 | 10/1986 | Kornberg . |
| 4,790,843 | 12/1988 | Carpenter . |
| 4,863,460 | 9/1989 | Magladry . |
| 4,865,600 | 9/1989 | Carpentier et al. ........... 623/2 |
| 5,071,431 | 12/1991 | Sauter . |
| 5,234,447 | 8/1993 | Kaster et al. ............... 606/153 |
| 5,306,296 | 4/1994 | Wright . |
| 5,397,348 | 3/1995 | Campbell . |
| 5,464,415 | 11/1995 | Chen ........................ 606/153 |
| 5,464,449 | 11/1995 | Ryan . |
| 5,554,162 | 9/1996 | DeLange ................... 606/153 |
| 5,571,116 | 11/1996 | Bolanos et al. ............. 606/151 |

*Primary Examiner*—Paul B. Prebilic
*Attorney, Agent, or Firm*—Terry M. Gernstein

[57] ABSTRACT

A heart valve can be replaced using minimally invasive methods which include a sutureless sewing cuff that and a fastener delivery tool that holds the cuff against the patient's tissue while delivering fasteners, two at a time in opposite directions, to attach the cuff to the tissue from the inside out. Drawstrings are operated from outside the patient's body and cinch the sewing cuff to the valve body. The cuff is releasably mounted on the tool. The tool stores a plurality of fasteners thereon. Two rows of staggered fasteners are formed whereby fasteners are located continuously throughout the entire circumference of the cuff. A minimally invasive surgical method is disclosed, and a method and tool are disclosed for repairing abdominal aortic aneurysms in a minimally invasive manner.

45 Claims, 20 Drawing Sheets

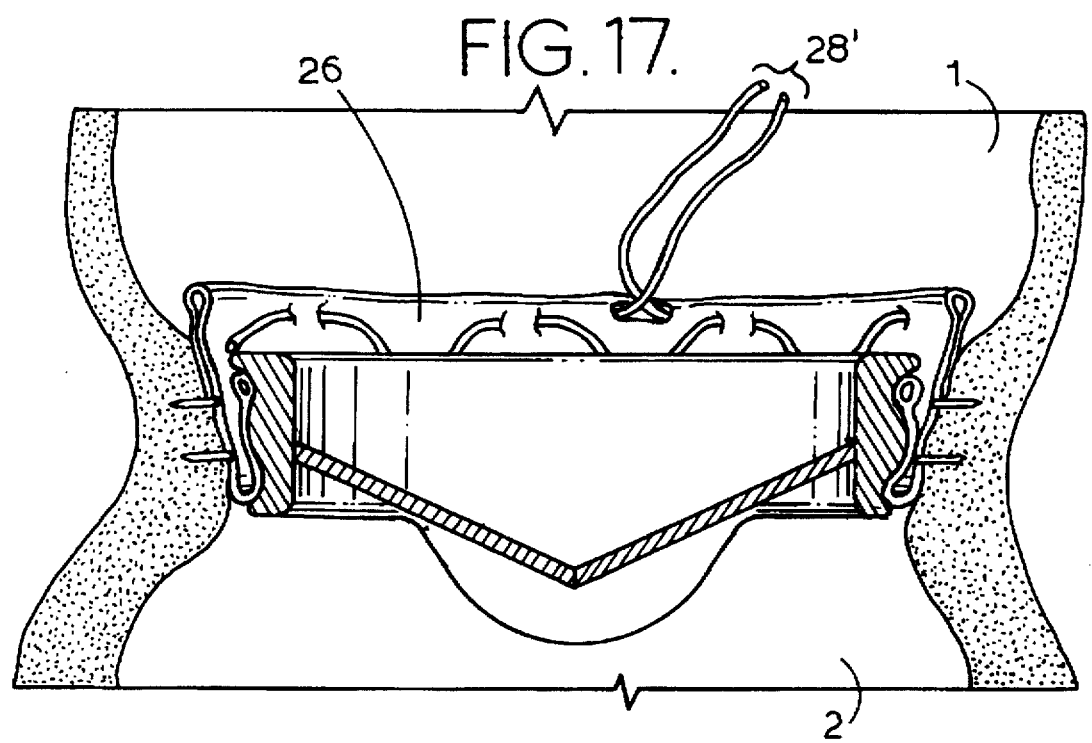
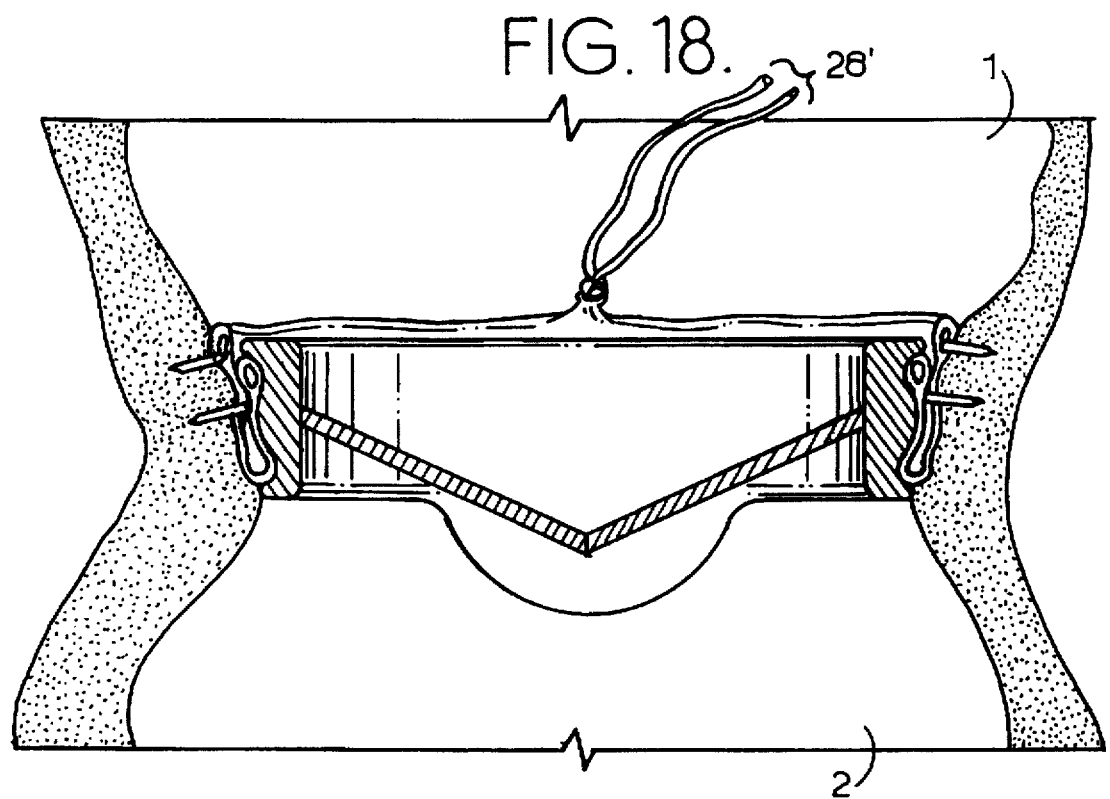

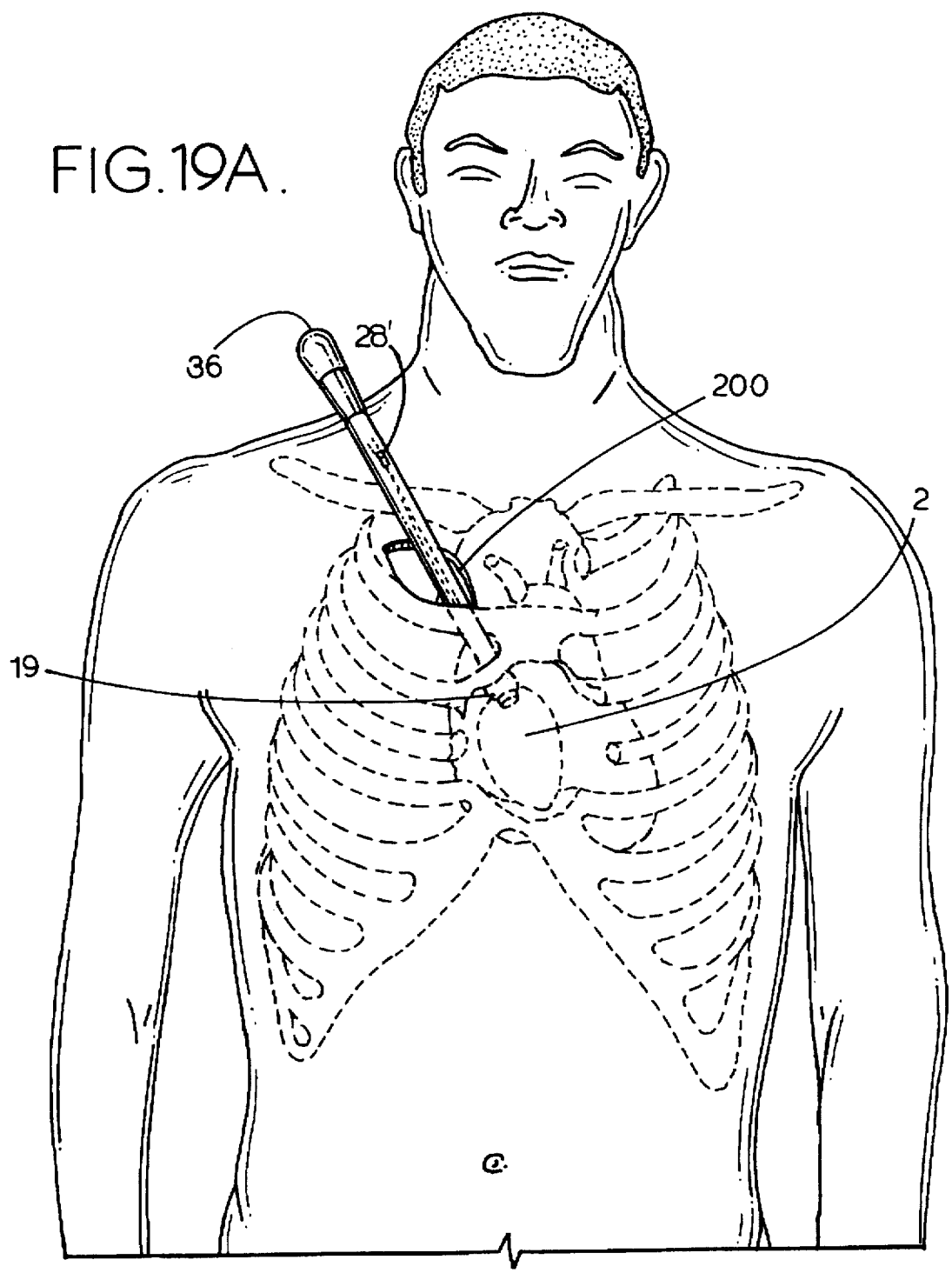

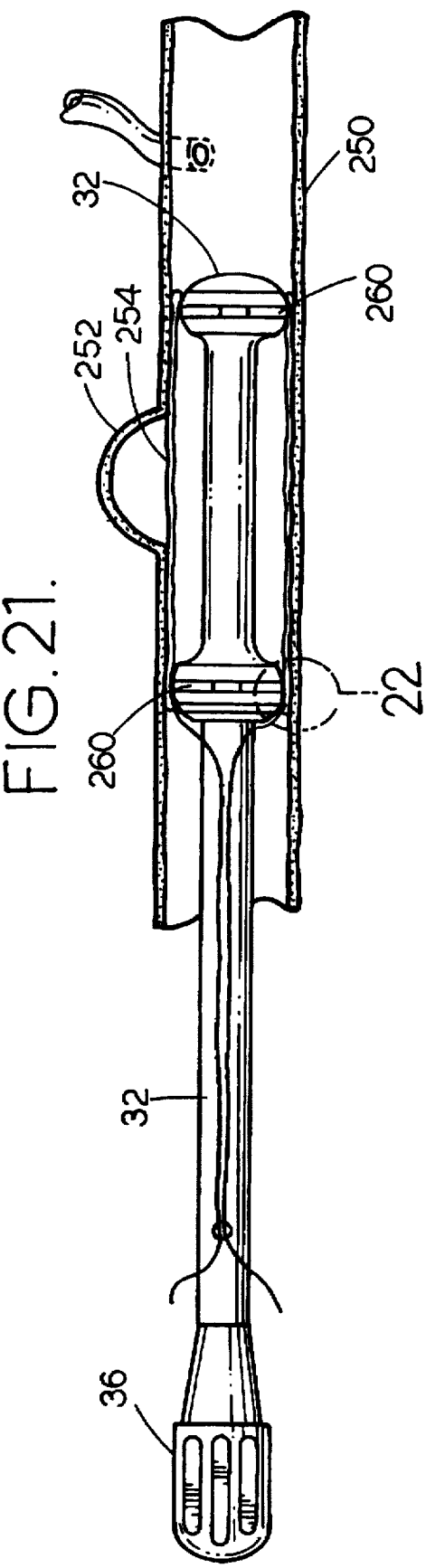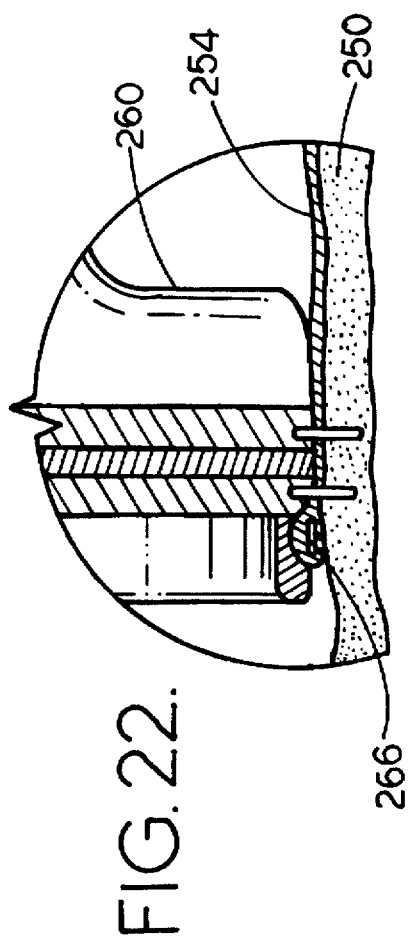

MEANS FOR REPLACING A HEART VALVE IN A MINIMALLY INVASIVE MANNER

TECHNICAL FIELD OF THE INVENTION

The present invention relates to the general art of prosthetic devices, and to the particular field of prosthetic heart valves and surgical tools and techniques associated therewith.

BACKGROUND OF THE INVENTION

It is well known that heart diseases may result in disorders of the cardiac valves. For example, diseases such as rheumatic fever can cause the shrinking or pulling apart of the valve orifice, while other diseases may result in endocarditis, an inflammation of the endocardium or lining membrane of the heart. The resulting defects in the valves hinder the normal functioning of the atrioventricular orifices and operation of the heart. More specifically, defects such as the narrowing of the valve stenosis and/or the defective closing of the valve, referred to as valvular insufficiency, result in an accumulation of blood in a heart cavity or regurgitation of blood past the valve. If uncorrected, prolonged valvular stenosis or insufficiency may cause damage to the heart muscle, which may eventually necessitate total valve replacement.

These defects may be associated with any of the cardiac valves. For example, if the mitral valve stenosis connecting the left auricle with the left ventricle narrows, blood will accumulate in the left auricle. Similarly, in the case of mitral insufficiency, the mitral valve does not close perfectly, and blood in the left ventricle is regurgitated past the closed mitral valve into the left auricle when the ventricle closes.

In many cases, complete valve replacement is required. Mechanical artificial heart valves for humans are frequently fabricated from titanium, prolitic carbon or tissue, including tissue from cows, pigs or humans. Such valves have been used because of their nonthrombogenic properties. Human blood does not coagulate on contact with such valves. Moreover, they are lightweight, hard and quite strong. Therefore, such valves have become widely accepted and used by many surgeons. Any new prosthetic valve or surgical technique associated therewith should account for this. One popular prosthetic valve includes such a hard body and a knit fabric sewing or suture cuff fixedly attached thereto as by drawstrings made of plastics-type material. The sewing cuff is sutured in place on the patient's tissue, and that tissue grows into the fabric providing a secure seal for the prosthetic valve. As will be discussed below, even though this is a widely accepted valve, there are problems and drawbacks.

A standard implantable mechanical heart valve usually has an annular valve housing or body to provide a passageway for blood. Occulders are mounted in the annular body and open or close the blood flow passageway. Usually there are one or two occulders, but occasionally triple occluder configurations have been proposed. On the outside of the valve body there is usually an external, circumferential surface configured as a groove. The purpose of this groove is to facilitate attachment of the above-discussed suture ring to the valve body.

As above mentioned, replacement of heart valves has become a widely accepted procedure. Currently, as many as eighty thousand heart valve prostheses are implanted in the United States alone. This procedure is very expensive. It requires the talents of a highly skilled surgeon, perfusionist and anesthesiologist as well as the supporting staff and equipment required to keep the patient on a heart/lung bypass machine during the operation. While this procedure currently works very well, operating time is still extensive and the longer the patient is on bypass equipment, the greater the risk to the patient. Furthermore, hand suturing is tedious and time consuming further lengthening the time the patient is on cardiopulmonary bypass and hypothermia. This may increase the chances of tissue damage to the patient.

Therefore, there is a need for a heart valve replacement procedure that reduces the surgical time required for the operation.

Still further, many currently used surgical techniques are invasive and often require breaking of bones. This increases the time and difficulty of the recovery. Therefore, there is a need to develop a prosthetic heart valve and a procedure for implanting same that reduces the invasiveness of this surgery.

As above mentioned, hand suturing of prosthetic heart valves in place is widely accepted. However, this requires the opening of the patient's chest wall to gain access to the aortic valve through a transverse incision in the ascending aorta. The distance from the incision down to the valve is usually two to two and one halve centimeters with an aortic lumen diameter of between seventeen and thirty millimeters. This creates a very long and narrow tube into which the surgeon must place sutures. While this is a tedious procedure in an "open chest" case, it is very challenging to accomplish through any small incision between the ribs or through a thoracic inlet, as would be required in any minimally invasive procedure. Therefore there is a need for a device and method that can secure the valve remotely from outside the chest wall.

A further problem associated with suturing some prostheses is that the valve is bulky and reduces the inside diameter of the valve body. A reduced inside diameter of the valve reduces the flow area of the valve resulting in increased transvalvular pressure gradients resulting in increased work for the heart muscle. A reduced flow area for such a valve may adversely influence blood flow characteristics associated with the valve, thereby adversely influencing the performance of the valve. This is very counter-productive to the clinical needs of the prosthesis. It is very hard to develop a mechanical valve that has the same flow characteristics of a living tissue valve. This is especially so of many existing multi-part prostheses. Even the so-called sutureless valves that have been disclosed in the art may have this problem. Heart valve designs have been directed toward minimizing the back pressure or restriction of forward flow by maximizing the cross-sectional area of the valve within a given outer diameter base. Housing attachment means within the valve base narrows the inside diameter of the valve body thereby creating adverse flow characteristics. Therefore, there is a need for a prosthetic valve which has the flow area thereof maximized. Reduced flow area may also result in rapid blood acceleration with a concomitant risk of red cell hemolysis and activation of sensitive enzyme systems such as the clotting system.

Yet a further problem with some prosthetic heart valves and the implanting procedures associated therewith, is that there are unwanted projections remaining on the implanted valve. This is especially so for valves that are sutured in place. Blood clots tend to form around foreign objects in the body. The body's natural defenses try to seal off any foreign material and make it non-threatening. However, there is a danger that the formed blood clots may dislodge into the patient's blood stream, which may cause a major problem.

The sutures used in many existing techniques to sew a cuff in place are knotted and cut off. This leaves raw edges exposed to the patient's blood stream. These raw edges of the cut off suture and knot provide surfaces for clot formation and provide potential for clots to break off into the bloodstream as they are newly formed. Loose clots in the bloodstream are dangerous for the patient as they have the potential for producing a stroke. Clots forming on sutures may also extend onto the valve and produce malfunctions by trapping the valve open or shut. It is common practice to treat a post-surgical patient with heparin or some other anticoagulant to minimize the production of clots. Therefore, there is a need for a prosthetic valve and surgical implanting process that minimizes the amount of foreign objects that remain exposed to the patient after the valve has been implanted. The exposed surfaces may also become a site of infection. Circulating bacteria may become attached and lead to infection at the valve. These infections are notoriously difficult to treat with antibiotics.

Yet another problem arises because it is difficult to effect a secure fit between the prosthesis and the patient's tissue. If there are gaps between the lumen and the valve, a leak may develop causing blood to bypass the valve. This can cause disastrous problems. Additionally, in many of the prostheses that are disclosed in the prior art as being sutureless, there is no way to ensure close approximation of the aortic lumen to the valve base prior to setting fasteners. This has allowed the lumen to pull away from the base and create the just-mentioned leak-generated problems. This is because anatomy is different from patient to patient. It is impossible to make the entire spectrum of valve bases to accommodate such differences in anatomy as would be required by some of the systems presently in use. Additionally, differences in diameter are not just in diameter of the lumen, but in the irregularities of the annulus where the valve is to be placed. Still further, disease and calcification can make the placement of known valves unmanageable. Whatever the cause of the imperfect fit between the prosthetic valve and the lumen, the variation in opening size and/or shape must be accounted for in placing the prosthesis. A securely anchored and tightly fit prosthesis is necessary for a successful outcome.

Furthermore, an improper fit between the prosthetic device and the lumen may greatly increase the duration of the operation or require corrective surgery to replace an improperly placed prosthesis.

Therefore, there is a need for a prosthesis valve that can be securely fit to a patient's lumen in an expeditious and reliable manner.

While the art contains several teachings which could be applied to one or more of the above-mentioned problems, such as the above-discussed cuffs, these disclosures have several drawbacks which are in addition to those already mentioned. For example, these prosthetic valves generally include a sewing ring or suture cuff that has some sort of stiffener therein. An example of such a stiffener is soft plastic. Plastic, even easily molded plastic, may require the patient's tissue to be severely handled and still have puckering even after great precautions have been taken. In this situation, stiffening elements may be more difficult to handle than fully flexible elements and may adversely affect the patient's tissue. Therefore, any new prosthesis valve should use a fully flexible material to attach that prosthesis to the patient to avoid the problems of unduly stressing the patient's tissue during the placement of the valve.

Dacron, Polyester and Teflon have been a very popular material for sewing cuffs. It is slightly stretchable, allowing it to be dilated. Needles readily pass through it without tearing or snagging the fabric fibers and the Dacron material has exceptional implant qualities with a proven track record of bioacceptance that allows ingrowth of endothelial cells. Due to its wide acceptance, it will be commercially advantageous to incorporate Dacron into any new prosthesis valve.

Therefore, there is a need for a prosthesis heart valve which can be tightly placed in a patient without requiring undue stressing of the patient's tissue.

There is yet additional need for a prosthesis heart valve which can have its size and shape expeditiously adjusted to produce a secure, non-leaking, fit to the particular patient, again without placing undue stress on the patient's tissue.

Still further, it is highly desirable for the surgeon to be able to adjust the orientation of the valve in situ. This will permit the prosthesis to be customized to the particular patient. While many known valves can be moved in place, there is still need for improvement in the ease and accuracy of such a step.

Still further, because the position of the junction between the coronary arteries and the aorta is variable, the choice of the location of the placement of the prosthesis should be as great as possible. The high profile of many of the finished sewing cuffs of the known devices severely limits this choice.

Still further, in many instances, it is advantageous for the surgeon to move the prosthesis into various positions relative to the sewing cuff. This will allow the valve to sit at the same level, above or below a certain level. For example, it might be advantageous to seat the valve cuff to be seated above the annulus to maximize the effective orifice area. It will be advantageous to be able to place the prosthesis in the most superior position without interference with the coronary arteries thereby allowing a larger diameter prosthesis to be placed. A lower profile cuff allows the surgeon to place the prosthesis as high as possible without interfering with the coronary artery junction.

Therefore, there is a need for a prosthetic heart valve that has a low profile finished cuff whereby the surgeon can have a greater choice in the superior/inferior placement of the prosthesis valve.

Current prosthetic valves are inefficient because the sewing cuff occupies part of the area available for flow through the valve. If a very small prosthesis is placed in the annulus, there can be a mismatch between the patient's cardiopulmonary requirements and the flow area of the valve. If a patient demands a high level of flow due to a larger size, a small sized valve may result in a significant transvalvular gradient. That is, the pressure in the left ventricle is considerably higher than the pressure in the aorta. This results in increased work for the left ventricular muscle and may predispose to myocardial failure.

If the surgeon suspects that the prosthesis placed is going to be too small, he may elect to enlarge the aortic root. Presently, this is accomplished by opening the aortic annulus opened perpendicular to the plane of the annulus in continuity to the aortomy. The incision is extended along the anterior leaflet of the mitral valve for a varying length. A patch of tissue or fabric material is then stitched to this incision to enlarge it. The procedure allows the insertion of a larger prosthesis into the newly enlarged annulus. However, there is an increased risk to the patient, principally because of the risk of bleeding from the suture line. This site is virtually inaccessible to repair after the aorta is closed.

Therefore, there is a need for a simpler way to expand the aortic annulus. Dilation is preferred, and thus, there is a further need to be able to expand the aortic annulus by dilation.

OBJECTS OF THE INVENTION

It is a main object of the present invention is to provide a prosthesis heart valve which can be implanted in a surgical procedure that is minimally invasive.

It is another object of the present invention to provide a prosthesis heart valve that can be implanted in an expeditious surgical procedure.

It is another object of the present invention to provide a prosthesis heart valve that can present the largest possible flow area to the patient.

It is another object of the present invention to provide a prosthesis heart valve that reduces the number of objects exposed to the patient after implantation.

It is another object of the present invention to provide a prosthesis heart valve which can be customized to the particular patient without placing undue stress on the patient's tissue.

It is another object of the present invention to provide a prosthesis heart valve which can utilize widely accepted materials while still realizing the advantages set forth herein.

It is another object of the present invention to provide a prosthesis heart valve which utilizes a fully flexible sewing cuff.

It is another object of the present invention to provide a prosthesis heart valve which can use a Dacron sewing cuff.

It is another object of the present invention to provide a prosthesis heart valve which has a finished cuff that has a low profile above the valve.

It is another object of the present invention to provide a prosthesis heart valve which eliminates suturing as a means for attaching the prosthetic device to the patient.

It is another object of the present invention to provide a surgical technique associated with the implanting of a prosthesis heart valve which is minimally invasive.

It is another object of the present invention to provide a surgical technique associated with the implanting of a prosthesis heart valve which is minimally invasive yet which is accurate, expeditious and results in a firmly, accurately and fixedly placed prosthetic device.

It is another object of the present invention to provide a surgical technique associated with the implanting of a prosthesis heart valve which reduces the amount of stress that is placed on the patient's tissue during the placement procedure.

It is another object of the present invention to provide a surgical technique associated with the implanting of a prosthesis heart valve which does not require opening the patient's chest wall.

It is another object of the present invention to provide a surgical technique associated with the implanting of a prosthesis heart valve which attaches the prosthesis valve with fasteners that are hidden inside the device whereby the chances of infection and thrombosis are significantly reduced.

It is a specific object of the present invention to provide a surgical technique associated with the implanting of a prosthesis heart valve which hides the fasteners inside the sewing cuff.

It is a specific object of the present invention to provide a surgical technique associated with the implanting of a prosthesis heart valve which significantly reduces the chances of the cuff puckering during the implanting procedure.

It is another specific object of the present invention to provide a surgical technique associated with the implanting of a prosthesis heart valve which dilates the graft or cuff and the lumen together to provide intimate contact during the fastening procedure.

It is another object of the present invention to provide a surgical technique associated with the implanting of a prosthesis heart valve which allows for endoscopic visualization of the placement of the valve in the heart.

It is another object of the present invention to provide a surgical technique associated with the implanting of a prosthesis heart valve which permits both dilation and placement of fasteners in a sewing ring or graft.

It is another object of the present invention to provide a surgical technique associated with the implanting of a prosthesis heart valve which assures secure attachment of the prosthetic device to the patient.

It is another object of the present invention to permit a surgeon to use a larger valve if such larger valve is indicated.

It is another object of the present invention to provide a means and method wherein the annulus of the aorta can be stretched as a prosthetic valve is being placed.

It is another object of the present invention to allow insertion of a larger prosthesis without opening the annulus and adding a patch.

It is another object of the present invention to provide a means and a method whereby annuloplasty can be performed.

It is another object of the present invention to provide a device that will allow the addition of standard suture's to repair or reinforce any area of potentially weak attachment of the suture ring to the annulus.

SUMMARY OF THE INVENTION

These, and other, objects are achieved by a sutureless prosthetic heart valve or graft which has a flexible sewing cuff stapled in place prior to placement of the heart valve body. The objects are also achieved by a tool and a surgical procedure for effecting placement of the prosthetic valve in a minimally invasive manner.

More specifically, the prosthetic valve includes a flexible sewing cuff, such as Dacron, or the like, which is stapled to heart tissue using a special tool that is inserted into the patient via an incision located in the thorax, either via a retrostenal approach or by removal or separation of the ribs. The tool releasably carries the cuff and includes means for continuously pressing the flexible cuff against the patient's tissue during the stapling procedure whereby the cuff is deformed rather than the tissue and puckering is essentially eliminated.

The cuff is attached to the valve body using drawstrings which extend outside the patient's body. The valve body is positioned in the in-situ cuff and the drawstrings are operated. Because the cuff is flexible, stretching of the tissue is minimized since inaccuracies are, at least, partially, absorbed by the flexible cuff.

The system disclosed herein should have improved blood flow and biological acceptance in the patient because suture knots and felt pledgets are not used. This provides additional advantages to use of this system due to a potentially reduced risk of stroke and infection post-surgery and potential for use of lower doses of anticoagulant and antibiotics post surgery.

Still further, due to the minimally invasive nature of the procedure, there is a possibility of applying the teachings of this invention to emergency procedures that may be performed outside of an operating room environment.

Yet another advantage of the present system is the low profile of the finished cuff above the valve base. This allows the surgeon greater choice in the superior/inferior placement of the valve. This is important because the position where the coronary arteries join the aorta is extremely variable. The low profile of the cuff allows for more distance between the cuff and the coronary junction.

Because the cuff of the present device is formed of material that has already been successful and is widely accepted, the commercial advantages associated with this device are enhanced.

Due to the surgical techniques that can be utilized with the present invention, it is possible to use video appliances, such as miniature video endoscopes.

The presently disclosed means and method can be used to perform annuloplasty where the cuff is fastened to an aorta above a leaky but salvageable human tricuspid valve. A ring is then inserted into the cuff to size the annulus and import a compressive force on the valve causing the leaflets to close more securely. The ring could be malleable metal or plastic to allow the surgeon to shape it correctly to impart forces in right area. This could be applied to mitral and other locations as well.

The placed cuff can be inspected by the surgeon to be sure that it is placed securely. If the surgeon decides that hand-placed sutures will be helpful, he can place such sutures as needed.

BRIEF DESCRIPTION OF THE DRAWING FIGURES

FIG. 17 shows the in-situ cuff with the valve body in place prior to attaching the valve body to the cuff.

FIG. 18 shows the cuff attached to the patient and to the valve body that has been moved from the FIG. 16 position to the FIG. 17 position.

FIG. 19A illustrates the torso of a patient having the prosthetic valve of the present invention being placed using a fastener driving tool of the present invention in a minimally invasive surgical procedure according to the teaching of the present invention.

FIG. 21 shows an alternative form of the tool having two fastener-delivering heads and which can be used to repair an aneurysm.

FIG. 22 is an exploded section of FIG. 21.

DETAILED DESCRIPTION OF THE PREFERRED EMBODIMENT OF THE INVENTION

Figure 1:
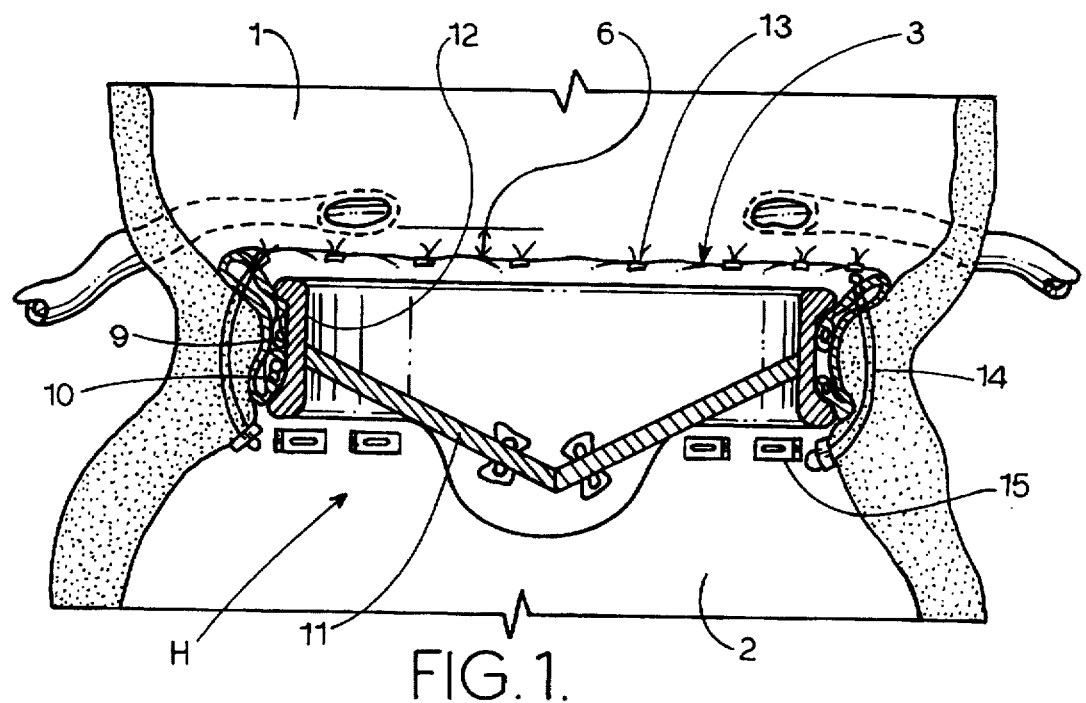
FIG. 1 shows a sectional view of a prior art prosthesis heart valve in place in a patient.

The invention is a device and method of fastening an aortic valve prosthesis or vascular graft, into living tissue, particularly suitable for minimally invasive surgery. In the preferred embodiment, the heart valve is separable from its sewing cuff. The valve body has special grooves in its periphery to allow the valve to be attached to the sewing cuff after it has been fastened into the annulus of the patient's aorta. The sewing cuff is specially constructed to provide a means to open up or unfold it and then detachably retain it to the fastener tool to allow for remote attachment of the cuff deep in the aortic lumen. Once the fasteners have been driven and the cuff is securely attached to the aortic annulus, the cuff attachment means is released and the fastener driver tool is removed from the heart. The prosthetic heart valve is then inserted into the aortic lumen and docked to the cuff. A special element is provided between the heart valve body and the cuff to signal to the surgeon when the valve body is properly seated in the in-situ cuff. An annular extension spring provides tension to hold the valve in place. It provides a tactile feedback which indicates to the surgeon that the valve body is securely attached to the cuff. Once the valve body is properly seated in the cuff, the cuff is attached to the valve body with drawstrings or the like. It is noted that while drawstrings are one means for attaching the cuff to the valve body, many other means, such as will be known to those skilled in the art based on this disclosure, can also be used without departing from the scope of this disclosure. Once tightly secured to the valve body, the cuff drawstrings are trimmed thereby completing the installation.

Currently-available valve replacements are hand sewn into the aorta after surgical removal of the defective valve. A critical component of the present invention is that the cuff is fastened to the living tissue with a series of metal fasteners or staples. The staples are arranged in two rows and are staggered to ensure a secure fit between the cuff and the tissue. The fastener driving tool has two stapling mechanisms on two different levels with the staple driving mechanisms on each level being spaced apart by 105° (see FIG. 11). The staples in each row are set two at a time, preferably 180° apart in each row, with both rows being set at the same time. The staple mechanisms in one row is off set from the staple mechanisms in the other row. After forming the two sets of opposed fasteners, the attachment tool is rotated. This automatically indexes to the proper fastener offset to create two staggered rows of fasteners. The offset between staple mechanisms in the two rows is preferably a 30° index and will provide twelve fasteners per row for a 19–21 mm aortic annulus. The fastener driver tool has means to dilate between standard size valve bodies. Thus, the same fastener driving tool can be used on all sizes from 19–23 mm and then the next size up would cover ranges from 23–27 mm, the next 27–32 mm and so forth. This is an important advantage because the surgeon will always want to place the largest body in the cuff. Presently, if a surgeon chooses a 19 mm valve and finds the cuff to be slightly loose in the annulus, it is a major expense to cut loose the 19 mm valve and try again with a 21 mm valve. The fastener driver tool of the present invention may include an indicator that indicates to the surgeon when he is fastening the cuff what size valve the annulus has been stretched to, thus eliminating guesswork.

Referring first to FIG. 1, a prior art prosthetic heart valve H is shown installed in the annulus of an aorta 1 next to a left ventricle 2. Valve H is secured in place by a series of sutures 14 which are tied in knots 13. The sutures are most often used with felt pledgets 15 to spread the load of the sutures evenly so as not to tear the tissue. Valve H includes a cuff 3 which is attached to the perimeter of base 12 of valve H in the factory. Drawstrings 9 and 10 are used to effect this attachment. The cuff and valve body are implanted as a single unit with the cuff being hand sewn to the tissue. Leaflets 11 are also shown as is the distance between the top plane of the valve and the right coronary artery junction with the aorta. This distance is indicated in FIG. 1 by numeral 6.

Figure 2:
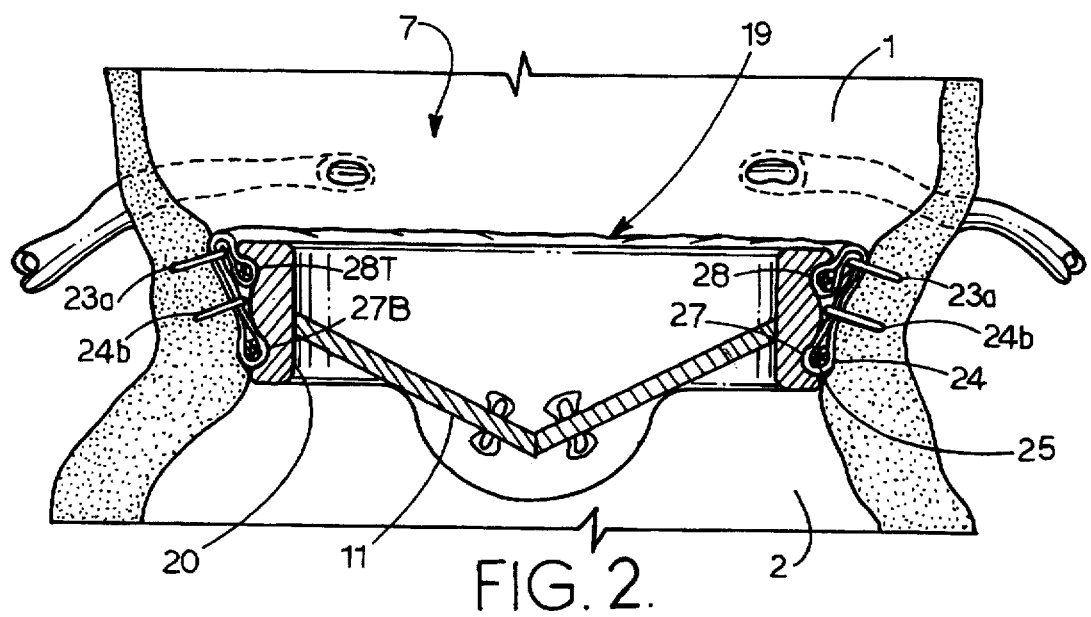
FIG. 2 is a sectional view of the prosthesis valve of the present invention installed in the aortic annulus of a patient.

Shown in FIG. 2 is a prosthetic valve 7 embodying the present invention installed and seated in the annulus of the left ventricle. Fasteners 23a and 24b are used to fasten sewing cuff 19 to the annulus of the aorta. The fasteners are staples in the preferred form of the invention. Drawstrings 27 and 28 are used to secure the cuff to the body 20 of the valve, and an indicating means 25, such as a garter spring or the like, is located in the lower section of the cuff. One form of the indicating means includes a garter spring inside a pocket in the cuff. Indicating means 25 is used to signal the surgeon when the heart valve body 20 has been seated properly in the cuff 19 prior to activating the drawstrings. Contact between means 25 and the valve body provides the surgeon with a tactile signal that the valve body is properly seated in the in-situ cuff.

As can be seen by comparing FIGS. 1 and 2, prosthetic device 7 has no sutures, no pledgets and will be installed as two parts—the cuff followed by the body; whereas, device H has sutures 14, pledgets 15 and is installed as a single unit. However, as can also be seen, the cuff in both instances is still securely connected to the valve body and the cuff can remain a flexible material, such as Dacron or the like whereby the surgeon will still be able to use familiar material. As will be discussed below, the cuff 19 is totally flexible so it can be deformed to fit the aorta rather than requiring the aorta to be deformed to fit the valve as is the case with the valve shown in FIG. 1. Still further, the fully flexible nature of the cuff 19 permits easy deformation of the cuff and thus significantly reduces stress on the tissue surrounding the prosthesis. Still further, the fully flexible nature of cuff 19 permits it to be pressed against the tissue at all times during the installation process so the chance of puckering or paravalvular leak paths is significantly reduced, if not completely eliminated. Using staples in place of the hand-set sutures of the prior art will, as will be understood from the present disclosure, permit the installation of valve 7 using a surgical technique that is minimally invasive.

Figure 3:
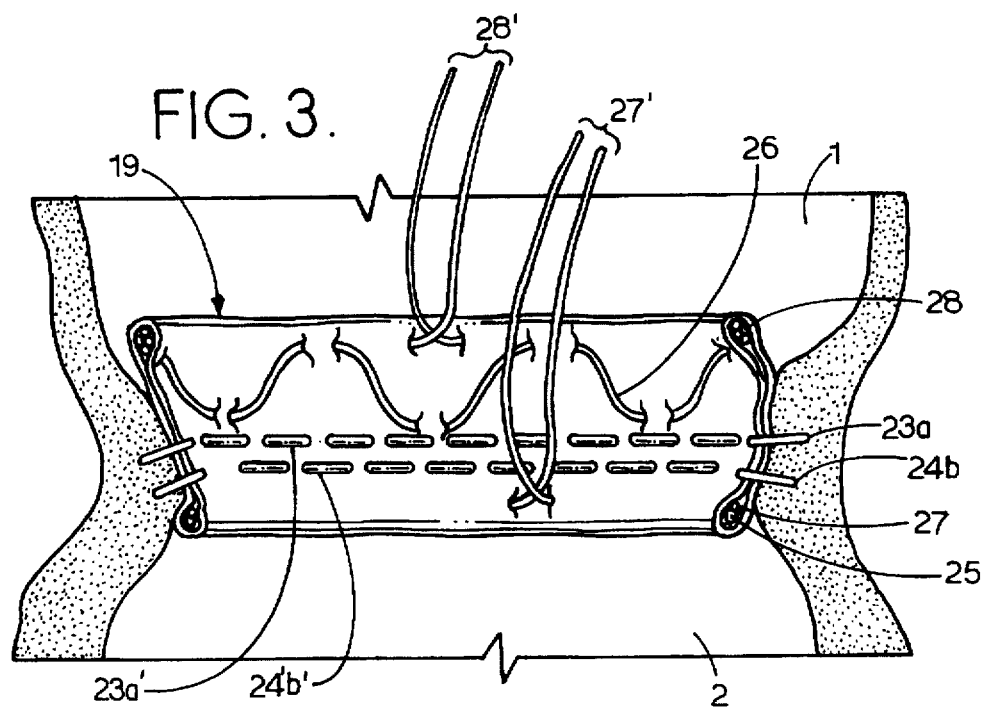
FIG. 3 is a sectional view of a sutureless cuff used in the present invention when the cuff has been stapled to the patient and prior to placement of the prosthetic valve body.

Cuff 19 is shown in place in the aorta prior to placement of the valve body in FIG. 3. Fasteners 23a and 24b are shown in two rows, with staples in one row being offset from corresponding staples in the other row. Thus, for example, staple 23a' in the top row corresponds to staple 24b' in the bottom row. The staggered nature of the staples in the two rows causes the cuff to be set by a continuous set of staples if the two rows are viewed together. That is, there is some portion of a fastener connecting the cuff to the tissue everywhere in the 360° of the circumference of the cuff. The two rows of staggered fasteners thus forms a means for connecting of the cuff to the tissue in a continuous manner about the entire perimeter of the cuff, and eliminates leak paths.

As shown in FIG. 3, the drawstrings 27 and 28 of valve 7 extend out of the cuff for a significant distance. As will be understood from this disclosure, these drawstrings have extensions 27' and 28' which extend out of the patient's body when the valve is being implanted. The extensions 27' and 28' are connected to the drawstrings 27 and 28 in the cuff which are means for fixedly attaching cuff 19 to body 20, and are actuating means attached to the drawstrings for operating the drawstrings from outside of the body after the sewing cuff has been attached to the patient to secure the cuff to the body 20. The prior art valve has no such drawstring extensions.

Figure 4:
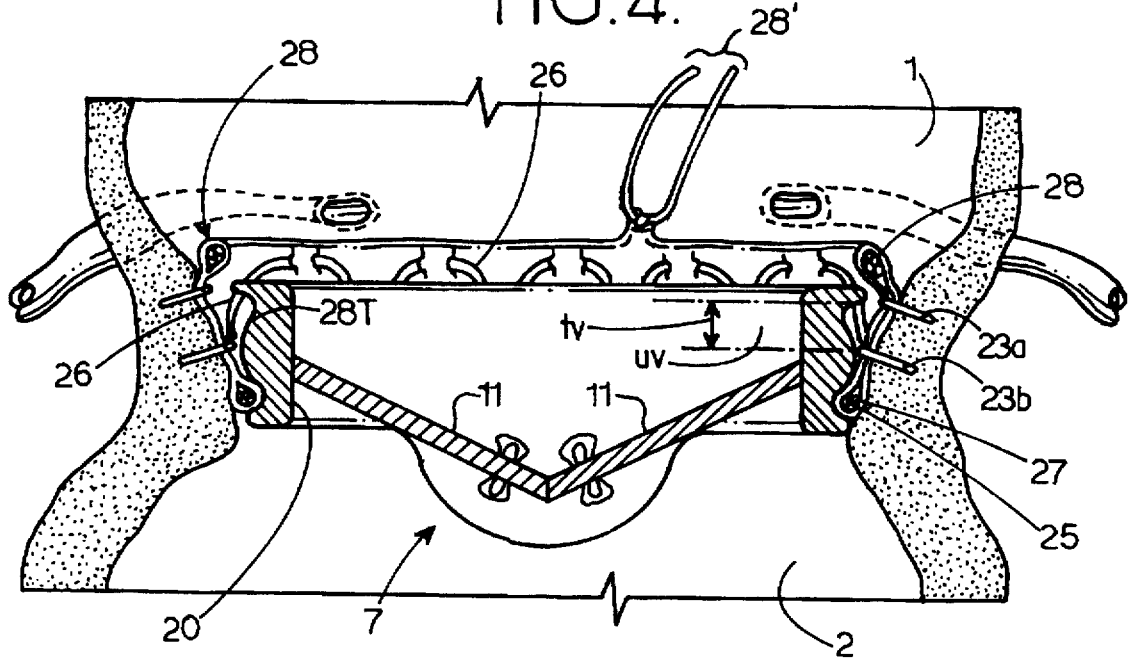
FIG. 4 is a sectional view of the prosthetic valve of the present invention after the cuff has been stapled in place and after the prosthetic valve body has been placed in the cuff and before the cuff is attached to the valve body.
Figure 5:
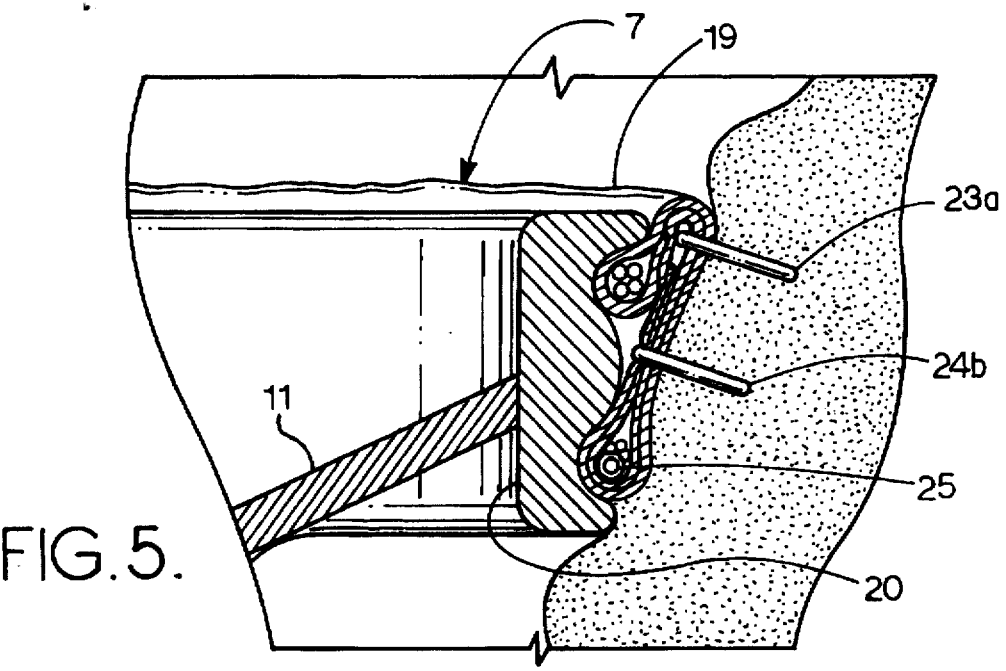
FIG. 5 is an enlarged sectional view of the sutureless prosthetic heart valve of the present invention with two rows of staples securing the cuff to the patient and the valve base attached to the cuff.

A zig-zag drawstring 26 is connected to extension 28' to be activated thereby. Drawstring 26 is sewn from top pouch 28 through the cuff and up again through the top pouch. When the activating means are activated, drawstring 29' is pulled and drawstrings 26 and 28 are activated when drawstring 27' is pulled, drawstring 27 is activated and drawstrings 27 and 28 are pulled into recesses in the body of the valve. The recesses are shown in FIG. 2 at 28T and 27B respectively. FIG. 4 illustrates how the cuff will be drawn into the recesses of the valve body during this cinching procedure. In the FIG. 4 condition, the top cords have not yet been seated. When the cords are pulled tight and cinched up the zig-zag drawstring will automatically pull the top cords down into the top recess. Further tightening will cinch the cords tight into the recesses. After tightening, knots can be defined in the cords to secure the means 27' and 28'. FIG. 5 shows the prosthesis after it has been set and the cuff attached to the body.

Figure 6:
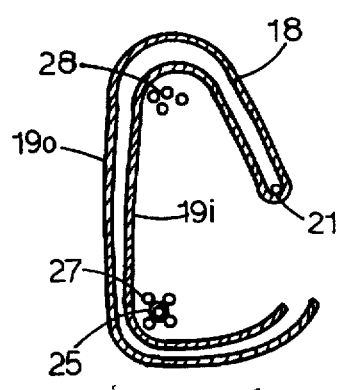
FIGS. 6, 7 and 8 illustrate how the sutureless cuff of the present invention is constructed.
Figure 7:
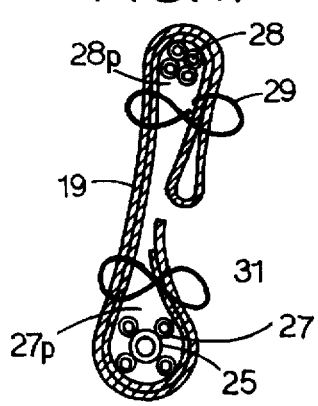
Figure 8:
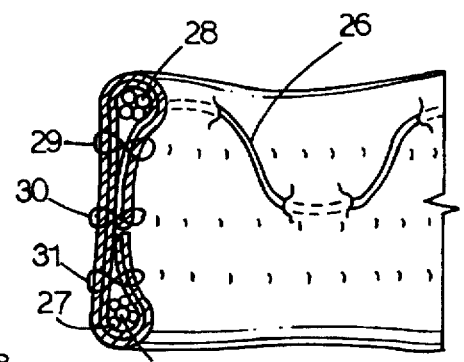

The sutureless cuff 19 is shown in FIGS. 6, 7 and 8. This cuff can be expanded for sizing. As shown in FIG. 6, the cuff is formed of a single, unitary tubular piece of fabric 18 which is folded over at location 21 to form an inner layer 19I and an outer layer 19O, with top cord 28 and bottom cord 27 being located at corners in the fabric. Cord 28 is adjacent to guide means 25. As shown in FIG. 7, stitching 29 and 31 create drawstring pouches 27P and 28P. A final suture stitch 30 is shown in FIG. 8 completes the cuff.

A tool T for placing the cuff in the patient and for applying the fasteners to attach the cuff to the patient is shown in FIGS. 9–16. This tool can be inserted into the patient to initially place the cuff in position, and to set the fasteners to attach the cuff. The tool is operated from outside the patient's body so the overall procedure is minimally invasive.

Figure 9:
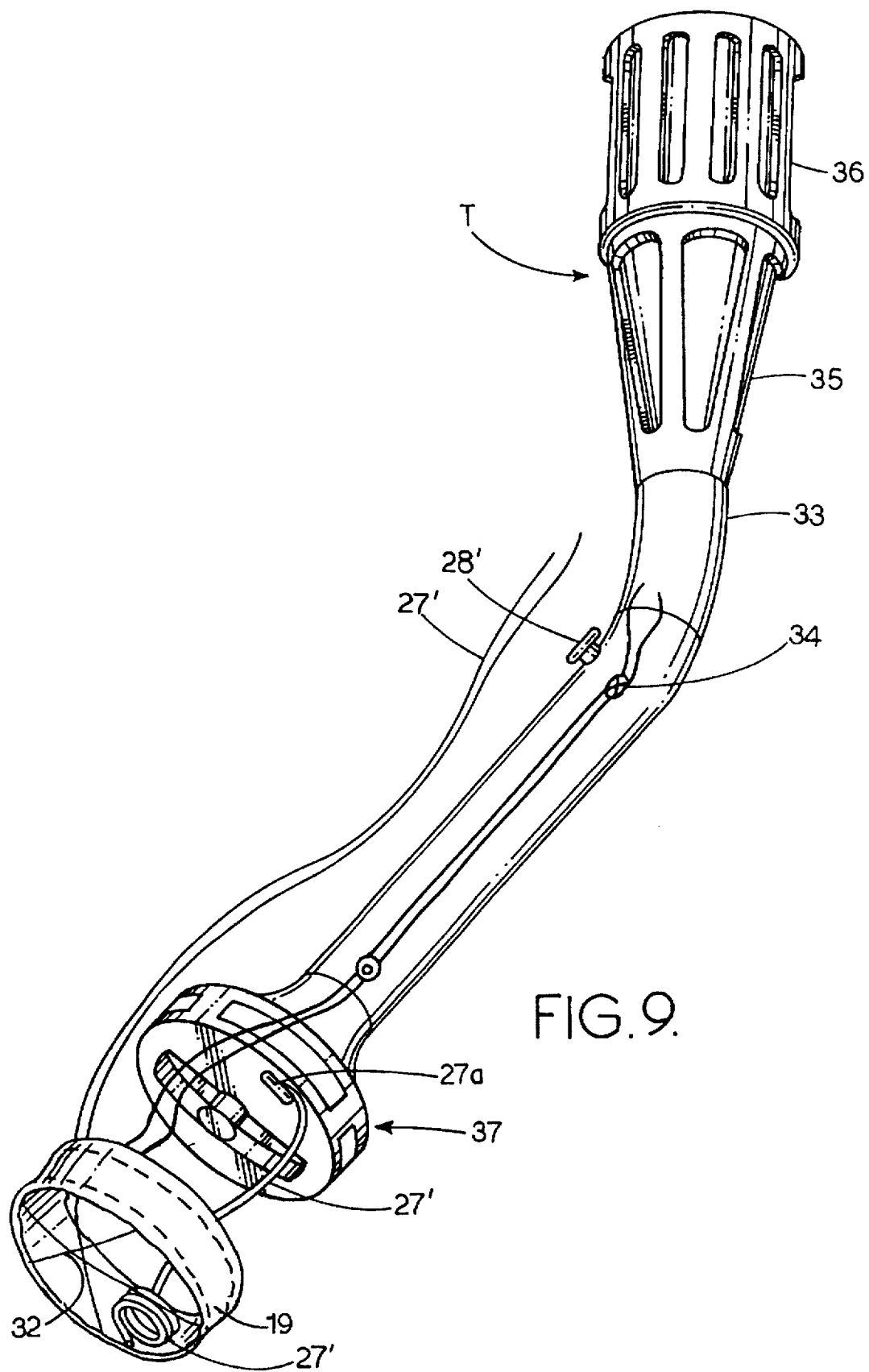
FIG. 9 is a side and bottom perspective view of a preferred form of a fastener driving tool used in the present invention.

Tool T broadly includes an operating handle 35 and a fastener deployment knob 36 on one end of a body 33 which can be curved if desired. An operating head 37 is on the other end of body 33. Anchor means 28a" are located adjacent to handle 35 and releasably attach the activating means 28' to the tool so these activating means are located outside of a patient's body during the cuff attaching procedure. As will be understood from the teaching of this disclosure, once the cuff is attached to the patient and the valve body is in place, the activating means are released from the tool and are operated to attach the cuff to the body. For the sake of clarity, the activating means are shown in FIG. 9 released from the tool. It is also noted that there will be a sleeve on the shaft to keep the drawstrings from winding up on the shaft. Alternatively, the drawstrings can extend through the center of the shaft or held in a coiled at the bottom of the tool.

Suture stays 32 are attached to the tool head 37, and the cuff is stretched over the head 37. The temporary suture stays 32 are drawn over the distal and proximal ends in order to secure the cuff to the head 37 during placement into the patient's body. The temporary suture stays 32 are tied to post 34 so that once the fasteners are deployed, the suture stays 32 can be cut to release the cuff 19 from the head 37 to help the surgeon with alignment of the body 20. The stays 32 act as a hammock or safety net to prevent the body 20 from being placed too low in the cuff which would result in the misalignment of lower drawstring 27 into the lower recess 27B. As deployment knob 36 is turned in a clockwise direction, each half revolution of the knob delivers two pairs of fasteners through the cuff. During that rotation, the latter part of the handle movement indexes head 37 inside the cuff 19 staggering the next pair of fasteners to be delivered. Drawstring activating means 28' is fed up along the shaft of the tool T to the holding cleats 28a" and are removed from this cleat, allowing tool T to be removed from the patient. Activation means 27' is retained coiled at the bottom of the instrument. The means 27' will be played out as the tool is removed from the patient whereby this means 27' will also be located outside the patient for activation.

The tool T has several functions. One function is to insert the cuff into the patient, another is to position the cuff in the patient, another is to fasten the cuff to the patient, and yet another is to hold the cuff securely against the patient's tissue during the fastening procedure. This last function is performed as a dilation and spreading procedure as will be understood from the teaching of this disclosure.

Figure 10:
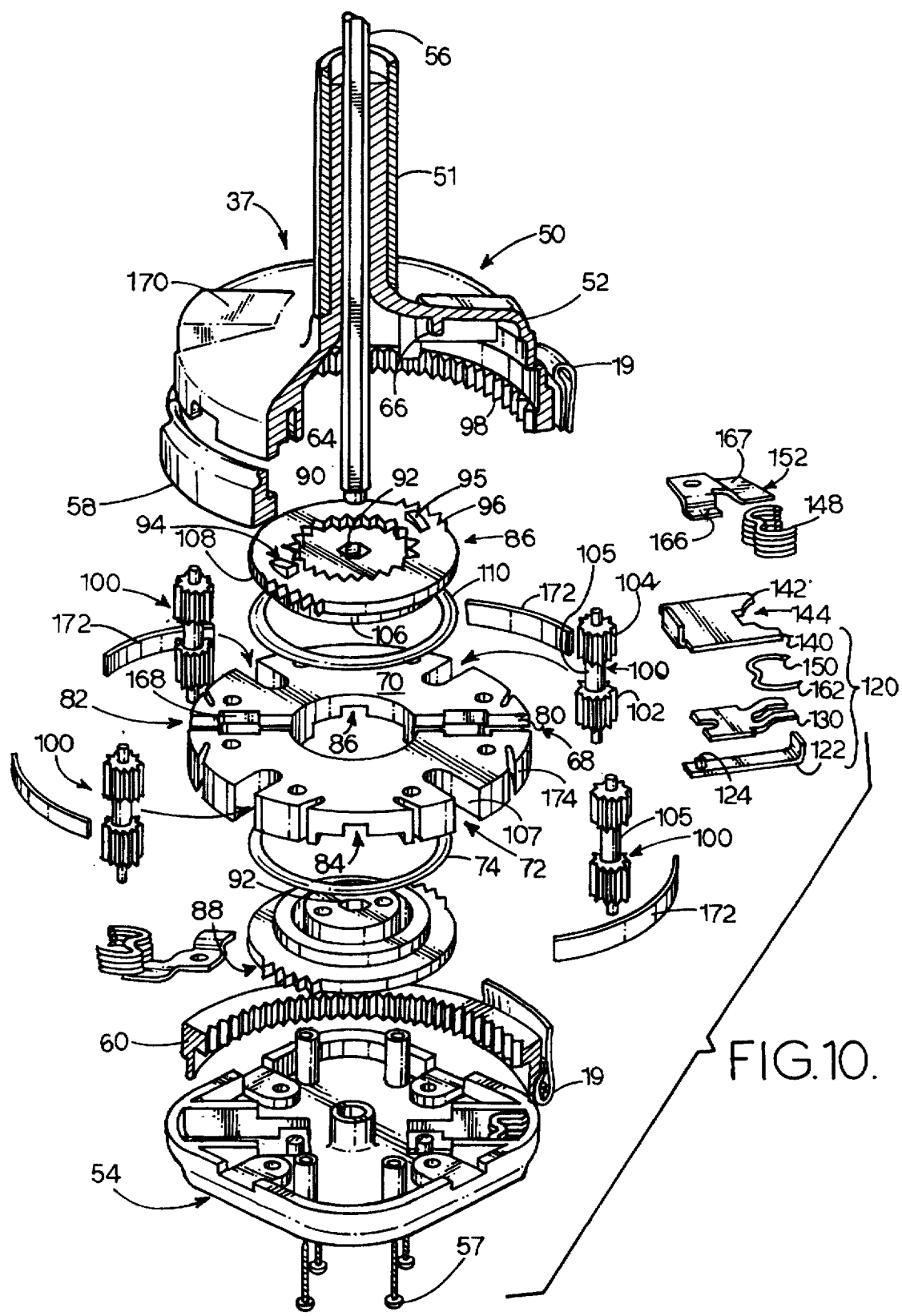
FIG. 10 is an exploded perspective view of the tool shown in FIG. 9.

Referring to FIG. 10, head 37 of tool T is shown as including a housing 50 which includes two sections, upper housing 52 and lower housing 54 both of which are attached to a hexagonally shaped drive shaft 56 and which are attached together by fasteners, such as screws 57. Drive shaft 56 is operatively connected to operating handle 36 to be rotated thereby. The housing sections are slidably connected to index rings 58 and 60 respectively and the cuff is connected to the index rings. As will be explained below, the housings are rotated during the fastening procedure, but the index rings remain stationary with respect to the housing so the cuff will remain stationary with respect to the housing. The index rings fit into grooves, such as groove 64, to be slidably connected to the housing sections. Upper housing 52 includes an anchor pin 66.

Also fixedly attached to the housing is a driver head plate 68 so that plate rotates with the housing. Plate 68 includes a top surface 70 and a bottom surface 72. Two identical fastener driver accommodating slots are defined on each surface of the driver head plate. These slots are identified in FIG. 10 by the reference numerals 80, 82, 84 and 86 and each extends radially of the plate. The slots are arranged so that top surface-located slots 80 and 82 are offset from each other by 180°, and bottom surface located slots are offset from each other by 180°, with the top surface-located slots being offset from the bottom surface located slots by 105°. After each fastener is set, the tool is rotated by 30° whereby the above-discussed stagger is established for the fasteners. The indexing of the head is achieved by movement of the handle 36 which is attached to a visually indicating means whereby a surgeon can keep track of where the fasteners are being set.

A cam means is located inside the housing. The cam means includes two cam plates, 86 and 88. The cam plates are identical, therefore, only one will be described. Cam plate 86 includes a top surface 90 and has a hexagonal hole 92 defined therethrough to attach the cam plate to drive shaft 56 for rotation therewith. An anti-retrograde means is included on cam plate 86 for preventing the cam plate from rotating in an undesired direction. Rotation in an undesired direction may interfere with the firm placement of the fasteners. The anti-retrograde means includes cleats 94 which are engaged by a one-way prong which permits rotation of the cam plate in one direction only. A second larger set of index lugs 95 can be provided to give feedback to the surgeon at the end of the fastener cycle. Index gear teeth 96 are defined on the outer peripheral edge of the cam plate and are operatively connected to index gear teeth 98 on the index ring 58 in a manner that rotates index ring 58 in a direction opposite to the direction of housing rotation at the same rate of rotation whereby the index ring remains stationary with respect to the patient as the housing rotates. This operation keeps the cuff, which is attached to the index ring, stationary with respect to the patient. Gears 96 and 98 are operatively coupled together by pinion 100 that is mounted at one end thereof on driver head plate 68 and at the other end thereof to the housing section 52, 54. Pinion 100 has a first gear teeth 102 engaging teeth 96 and second gear teeth 104 engaging gear teeth 98 for transmitting rotation of the cam plate to the index ring. Each pinion has a waist section 105 that is received in a pinion slot 107 defined in driver plate 68.

Figure 11:
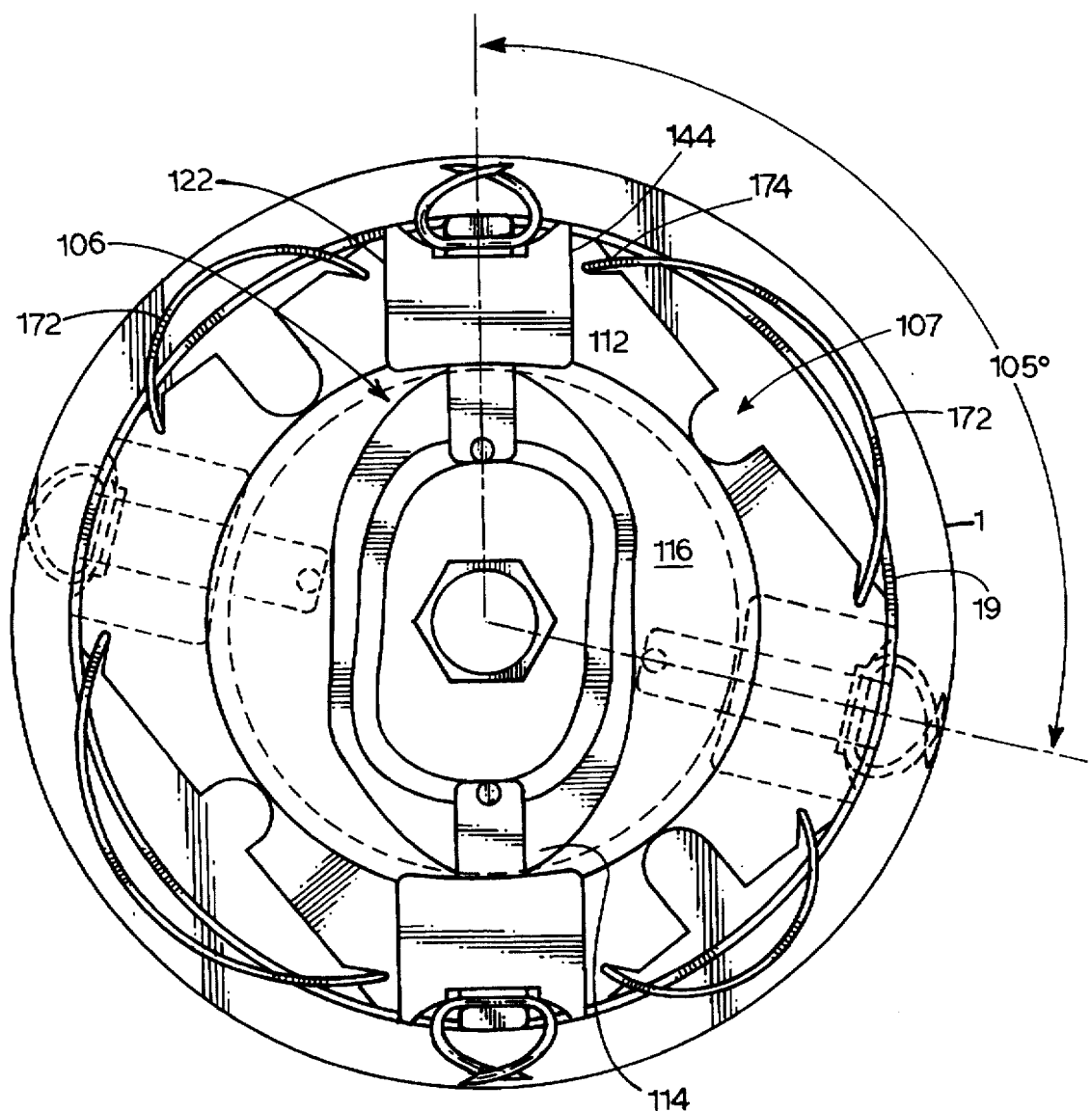
FIGS. 11, 12, 13 and 14 illustrate the various positions of the staple driving mechanism during operation of the fastener driving tool of the present invention.
Figure 14:
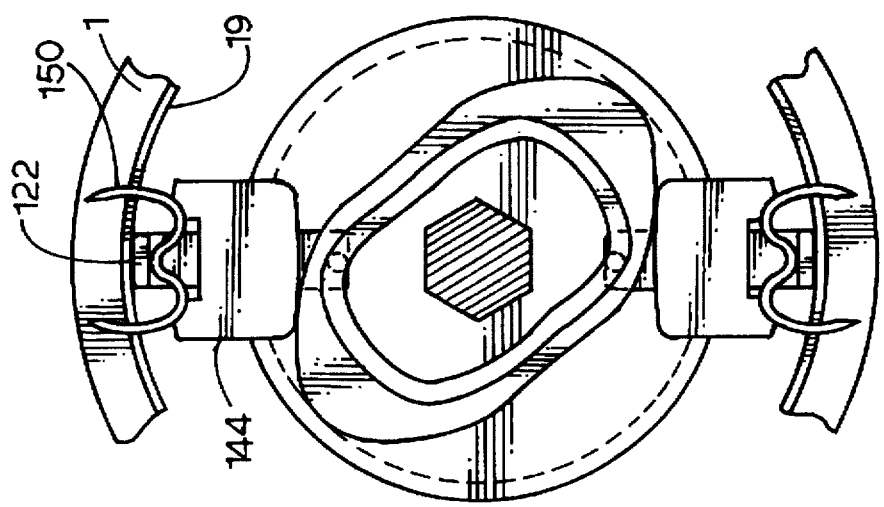
Figure 13:
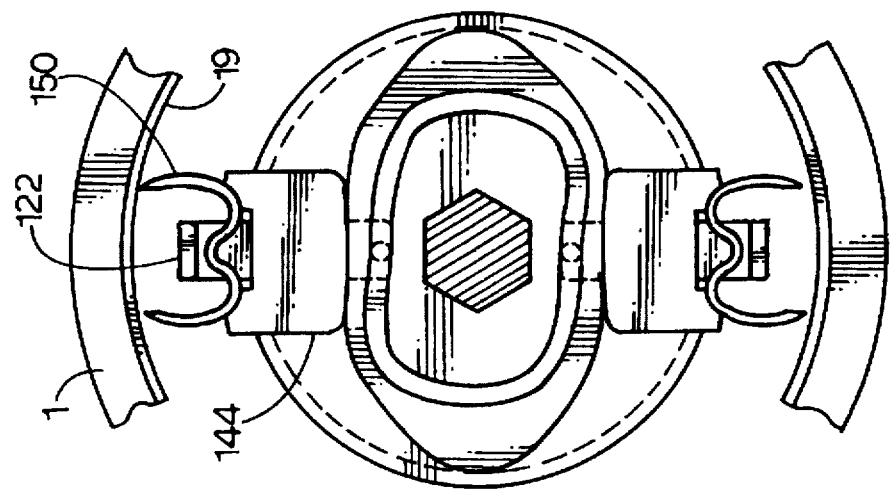
Figure 12:
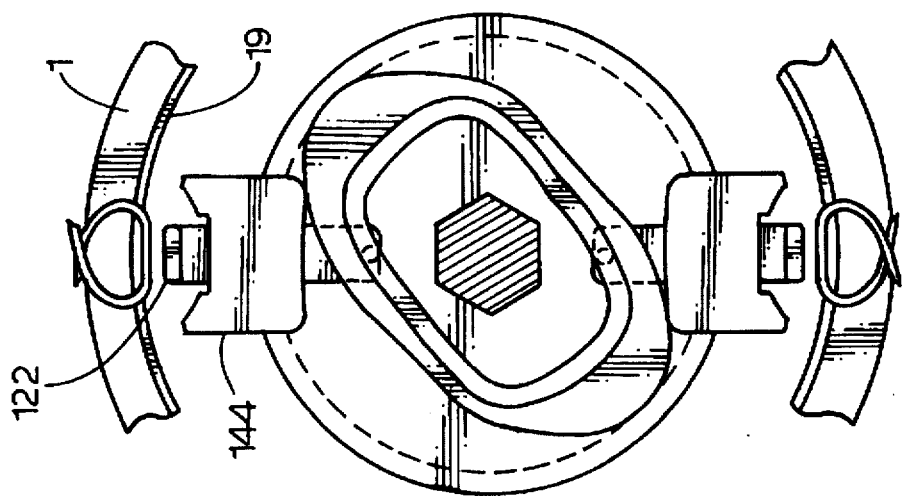
Figure 15:
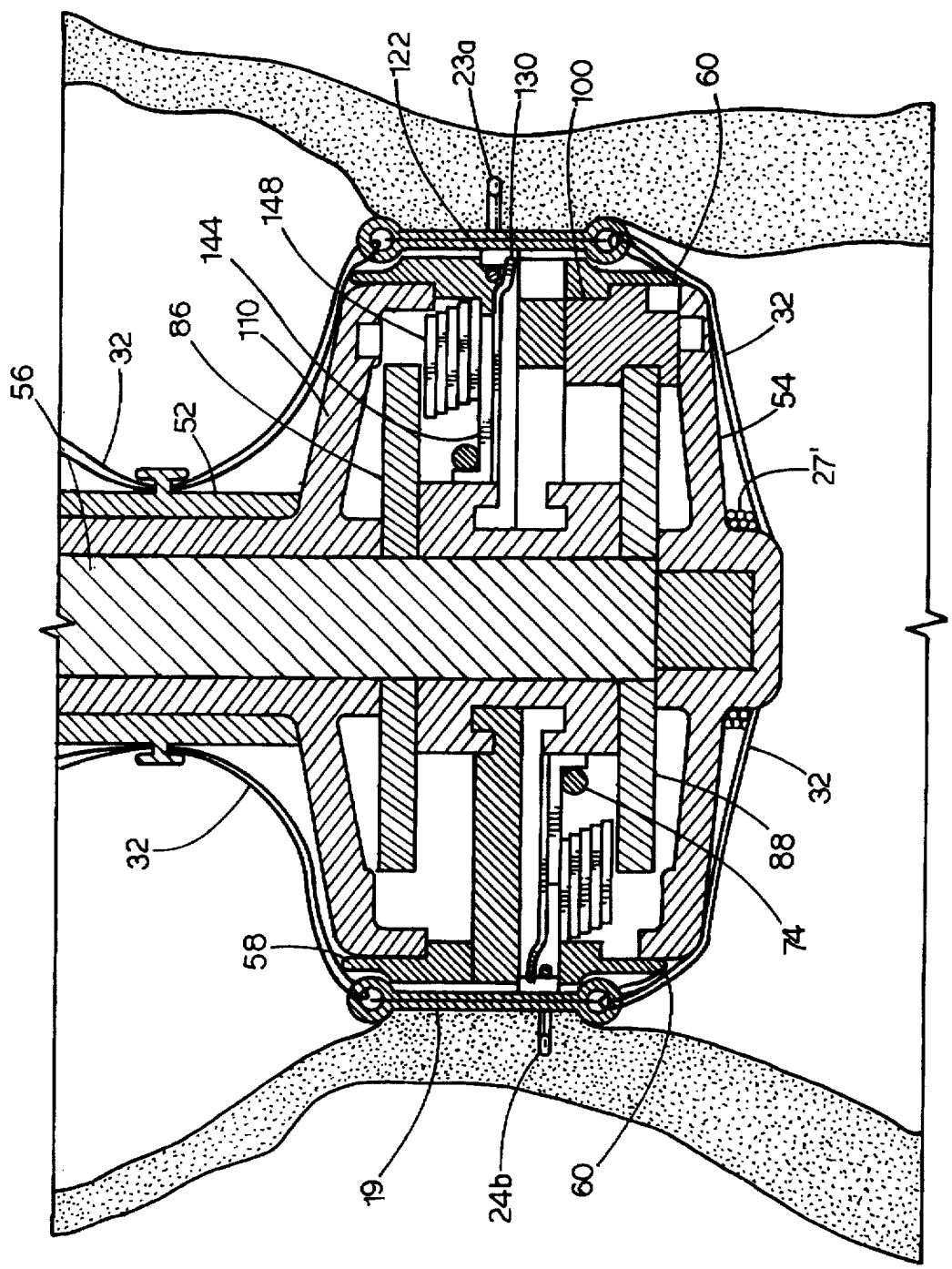
FIG. 15 is a sectional view of the fastener driving tool in the assembled condition.

A cam 106 is mounted on surface 108 of cam plate 90 and has an elastomeric band 110 thereon. The cam 106 is shown in FIGS. 10-12 and rotates with the cam plate. The cam has two lobes, 112 and 114 spaced apart by 180° as well as a groove 116 defined therein for a purpose that will be understood from the ensuing disclosure. The cams are rotated with respect to the driver head plate 68 whereby each cam lobe passes each slot 80 and 82 once each revolution of the drive shaft 56. As will be understood, each revolution of drive shaft 56 thus drives two fasteners from the top surface of driver plate and two fasteners from the bottom of the driver plate. In this manner, even pressure is placed on the cuff and tissue during each fastener driving step because the slots are offset from each other by 180° on each surface of the driver plate. This keeps the cuff and tissue from puckering due to unbalanced fastener driving forces.

Each of the slots 80, 82, 84 and 86 has a fastener driver mechanism 120 accommodated therein. All of the fastener driver mechanisms are identical, therefore, only one mechanism 120 will be described. Mechanism 120 includes an anvil 122 mounted on driver plate 68 to slide thereon, with movement of the anvil in a direction that is longitudinal with respect to the anvil being radial with respect to the driver plate. The anvil includes a pin 124 that is slidably received in groove 116 defined in the cam so the anvil is moved into and out of the slot as the cam rotates. This anvil movement is timed so fasteners can be driven without jamming. A lifter spring 130 is mounted under the driver plate to remain stationary on that plate whereby the anvil moves with respect to the lifter spring. A driver 144 is slidably mounted in the slot and is attached to the cam lobe by ring 110 engaging both the cam lobe and a rider 111. The driver moves radially of the driver plate and is held against chordal movement with respect to that driver plate. Therefore, rotation of the cam plate moves the driver 144 radially inwardly and radially outwardly with respect to plate 68. The groove 116 is formed so that driver and anvil movements are in timed relation to each other. The driver includes two fastener-engaging tips 140 and 142 which are separated by a U-shaped opening 144 having an anvil-receiving notch 146 located therein.

A stack 148 of fasteners, such as staple 150, is contained in the housing to feed fasteners between the driver head and the anvil in a manner that is timed to place a fastener in driving position prior to the driver head moving radially outward in a fastener driving movement. Opening 144 is sized and shaped so that lifter spring 130 moves a driven fastener off of the anvil prior to the anvil moving arcuately away from the driving location and prior to a new fastener moving into the driving position between the driver and the anvil. A stack spring 152 is anchored to the housing section 52 by projection 66 and maintains force on the fasteners that is directed to feeding fasteners to a fastener-setting location after a previous fastener has been driven through the cuff and into the tissue. The anvil folds the fastener in a manner such that the sharp points 162 of the fastener drive directly through the cuff and the tissue rather than tear through the cuff and tissue. The anvil then folds the fastener after that fastener has pierced the cuff and the tissue to establish the closed fastener. Each stack spring also has an anti-retrograde spring 166 thereon. Spring 166 engages cleats 94 on the cam to prevent the cam from moving in an undesired retrograde direction. Fasteners are retained into the housing via recesses or doors, such as pocket 170. Each stack spring 152 also has two wings 167 that engage slots 168 defined in the driver plate to maintain the stack spring in the proper orientation and position to feed the fasteners, yet which will permit the stack spring to be removed via the door 170 to load fasteners. However, the preferred form of the tool is disposable.

As above discussed, it is a significant advantage of the tool T that the cuff is maintained in constant contact with the tissue during the fastener setting procedure. This advantage is realized by means of cuff dilation means, such as spring 172, mounted on the driver plate and extending radially outward from the outer peripheral edge of that driver plate. The springs curve gently outward and inward in a U shape to gently engage the cuff from the inside of that cuff and gently urge it against the tissue. The springs are mounted on the driver plate by spring-receiving slots, such as slot 174, defined in the outer peripheral edge of the driver plate so the spring is maintained on the plate and in the desired orientation.

For purposes of clarity, four positions of the fastener driver mechanism are shown in FIGS. 11, 12, 13 and 14. Beginning a cycle, a fastener has been driven through the cuff and the adjacent tissue, and is formed in FIG. 11 when the driver forces the fastener against the anvil. As the drive shaft is further rotated, the cam lobe moves from the FIG. 11 position to a retracted position shown in FIG. 12, with the anvil being pulled back after the set fastener has been pushed off that anvil by the lifter spring 130. Continued rotation of the drive shaft rotates the cam lobe into a loading position shown in FIG. 13 during which time, a new fastener is fed between the anvil and the driver. Further rotation of the drive shaft rotates the cam into an advance position shown in FIG. 14 which forces the driver against the fastener and the fastener through the cuff and the tissue.

Once all of the fasteners have been set, sutures 32 are unfastened from the cleat 34 on the body 33, cut and loosened to permit the tool to be removed from the patient. Then means 28' is removed from the cleat on the tool. Then, tool T is removed from the patient which plays out activating means 27' to the outside of the patient. A prosthetic valve body 20 is then inserted into the patient using a tool 85 shown in FIG. 20, and is placed in position adjacent to the cuff. The valve body is moved until the surgeon is notified by the indicating means that the body is in the desired orientation. The activating means 27' and 28' are then activated to pull the cuff over and against the body by the above-discussed action of the drawstrings. Once the drawstrings are operated and the cuff is held tightly against the body 20, the activating means can be severed and removed from the patient. The prosthetic valve is now in place. Any tools can be removed from the patient and closure can be effected. As above discussed, the fasteners will be continuous over the entire perimeter of the cuff thereby further ensuring that no leak paths will develop. The continuous nature of the fastener coverage is best understood by visualizing a unit vector UV as shown in FIGS. 3 and 4, which is centered at the center of the cuff and being two rows thick, that is having a thickness indicated in FIGS. 3 and 4 by dimension $t_v$. As this unit vector moves through 360°, it will never be out of contact with a fastener whereby the entire circumference of the cuff is fastened to the tissue. The horizontal orientation of the fasteners further contributes to this feature.

Figure 20:
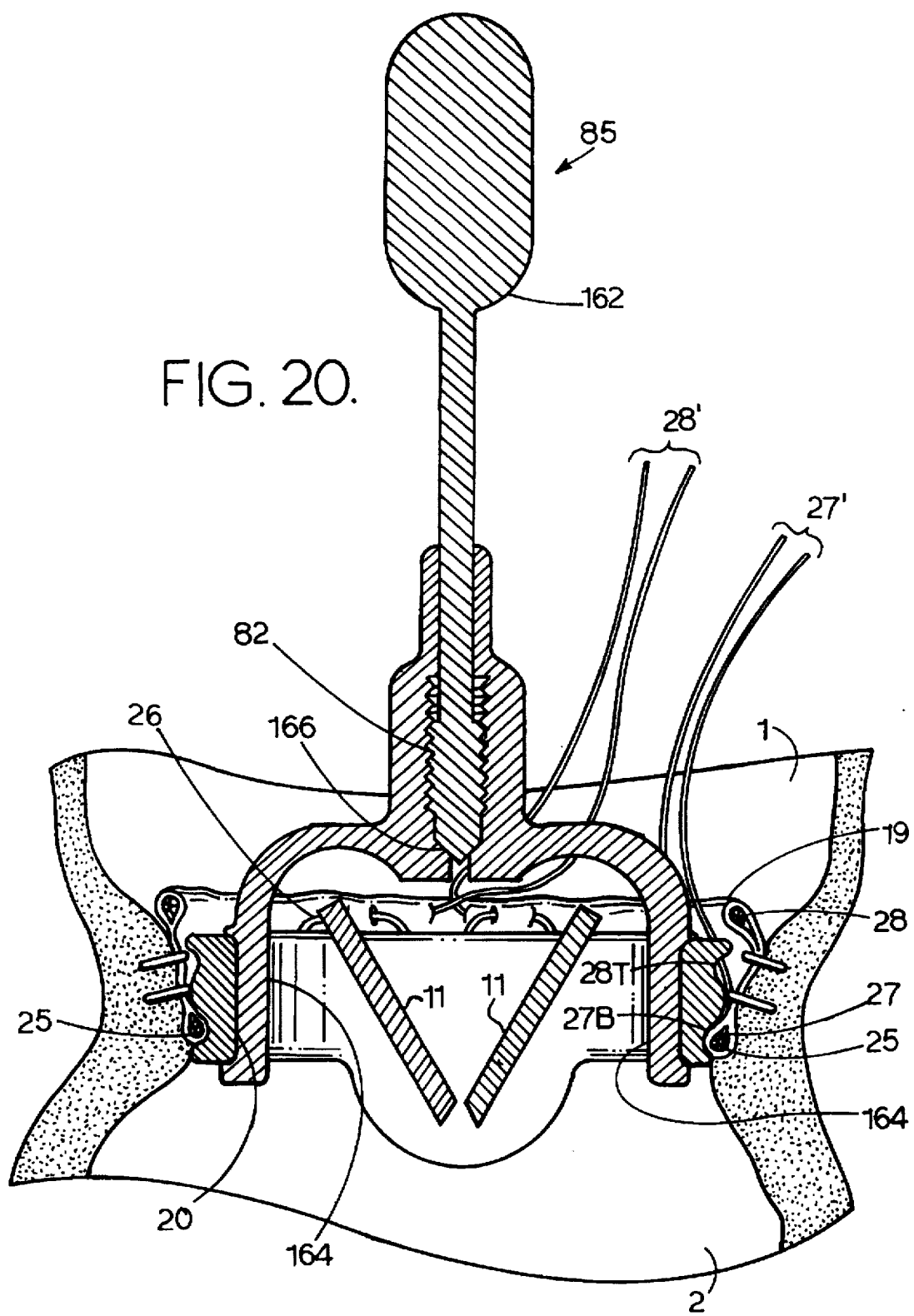
FIG. 20 shows a valve body holding tool inserting a valve body into an in-situ cuff.

As shown in FIG. 20, tool 85 includes a handle 162 and a pair of legs 164 which are spread apart by screwing handle 162 into the bottom of a holding fixture 164, forcing tapered edge 166 into the legs. The valve may then be inserted down into the cuff 19 until the garter spring 25 in the cuff is felt to detent into the lower recess 27B indicating proper seating of the valve body in the cuff.

Figure 16:
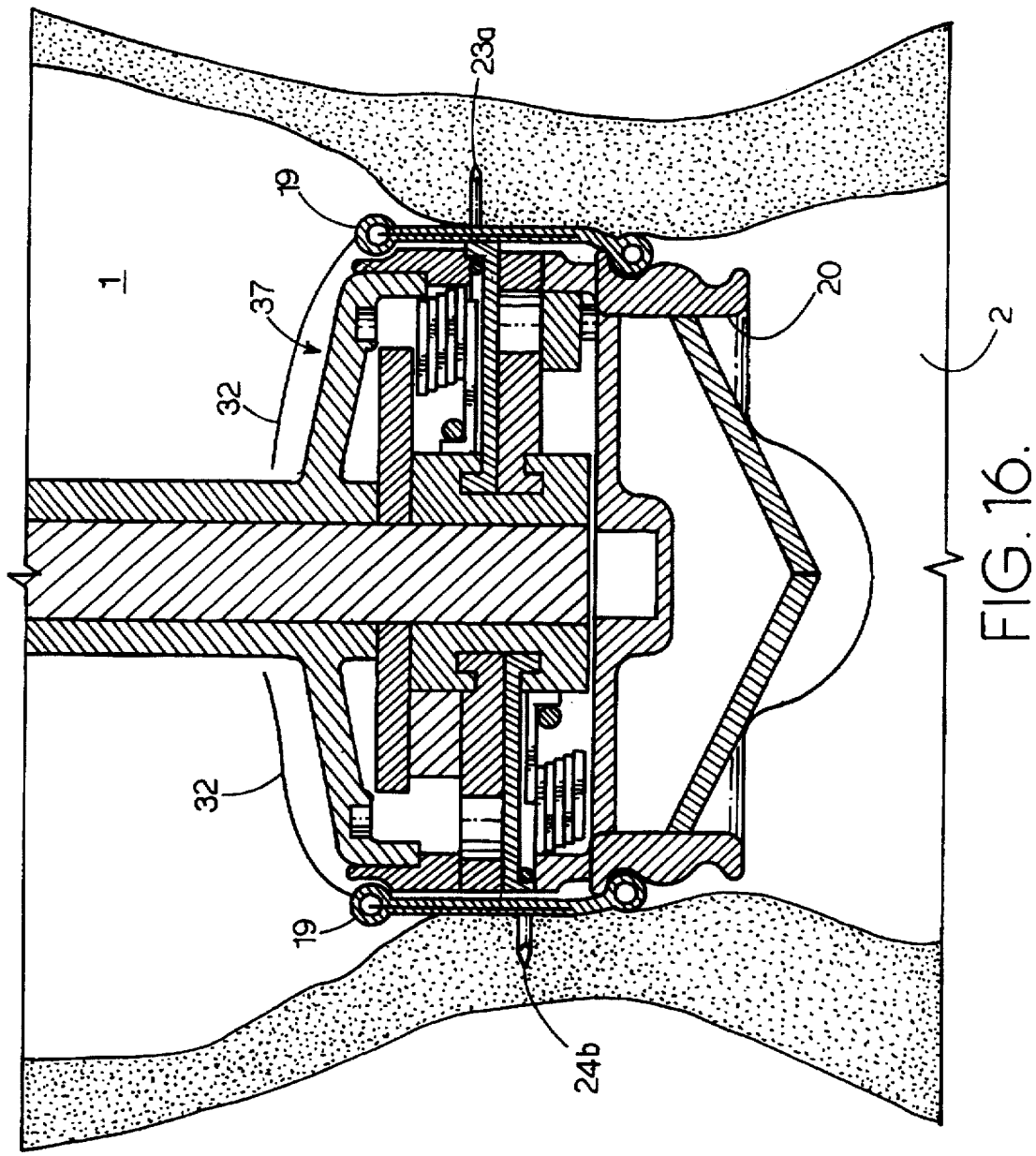
FIG. 16 shows the fastener driving tool in position after the cuff has been stapled to the patient and prior to movement of the valve body into position in the in-situ cuff.

An alternative form of the tool is shown in FIGS. 16–18 and maintains contact between the tool and the cuff whereby the cuff can be inverted after the valve body has been moved into position. The valve body is attached to the tool and to the cuff during fastening of the cuff to the tissue. After completion of the fastening step, the valve is pulled up thereby inverting the lower section of the cuff. The drawstrings are then cinched as above described.

Figure 28:
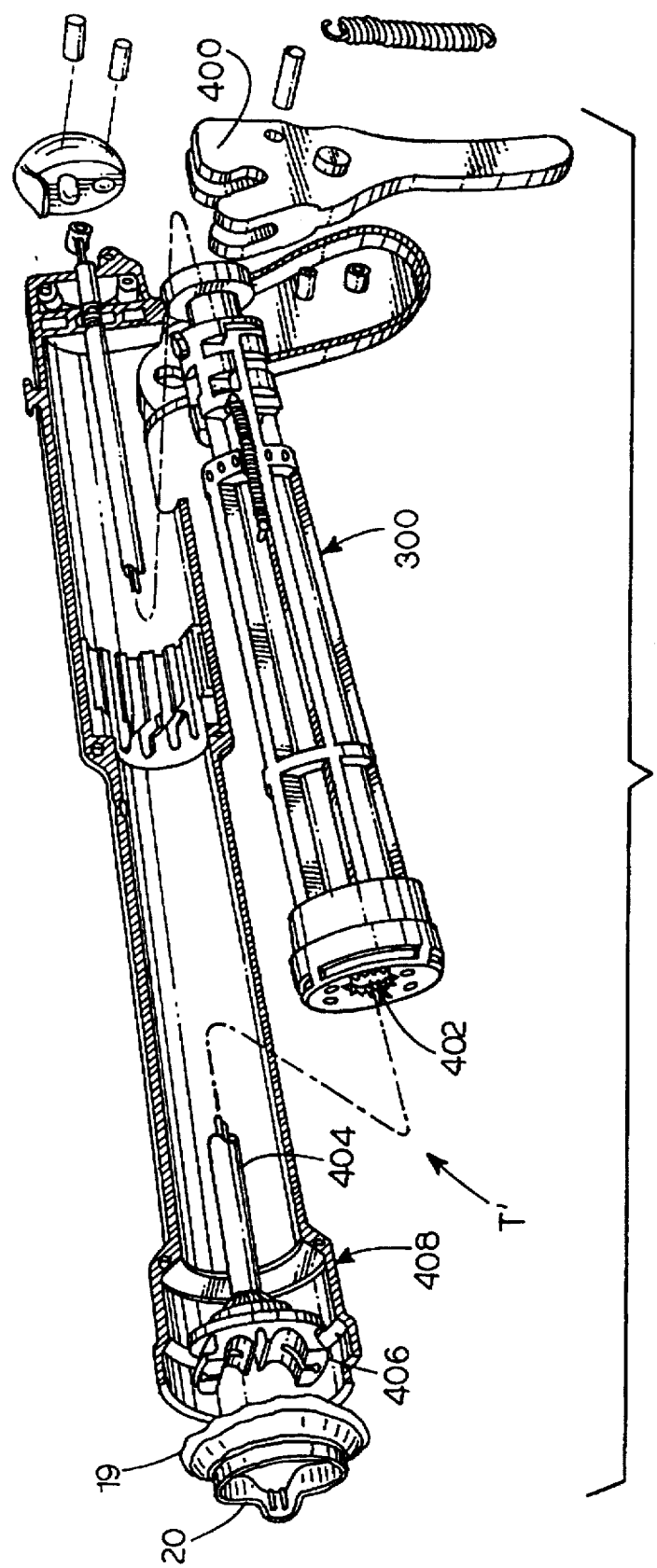
FIG. 28 is an exploded perspective view of another form of the tool which maintains the handle and shaft stationary during fastener delivery.
Figure 29:
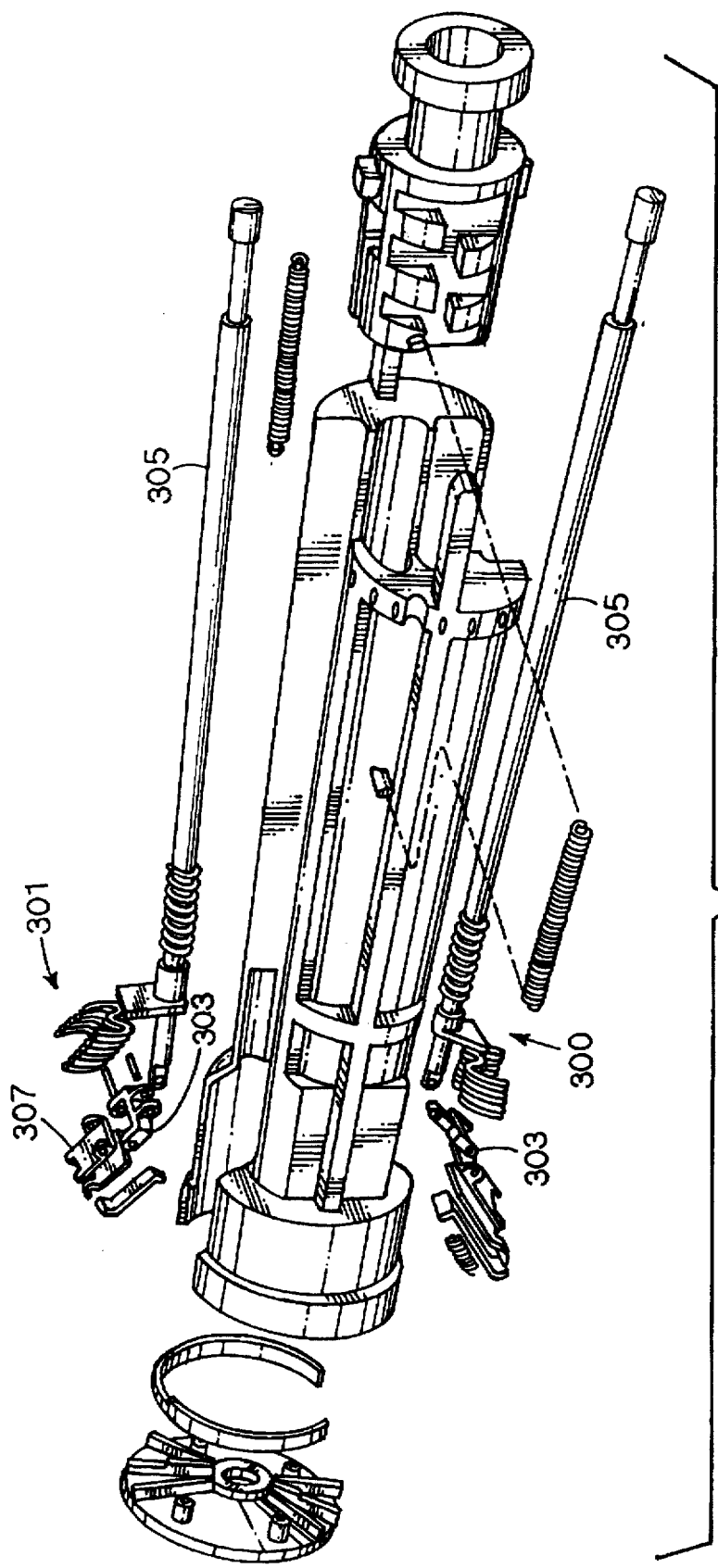
FIG. 29 illustrates a rotating fastener assembly for use in the tool shown in FIG. 28.
Figure 30:
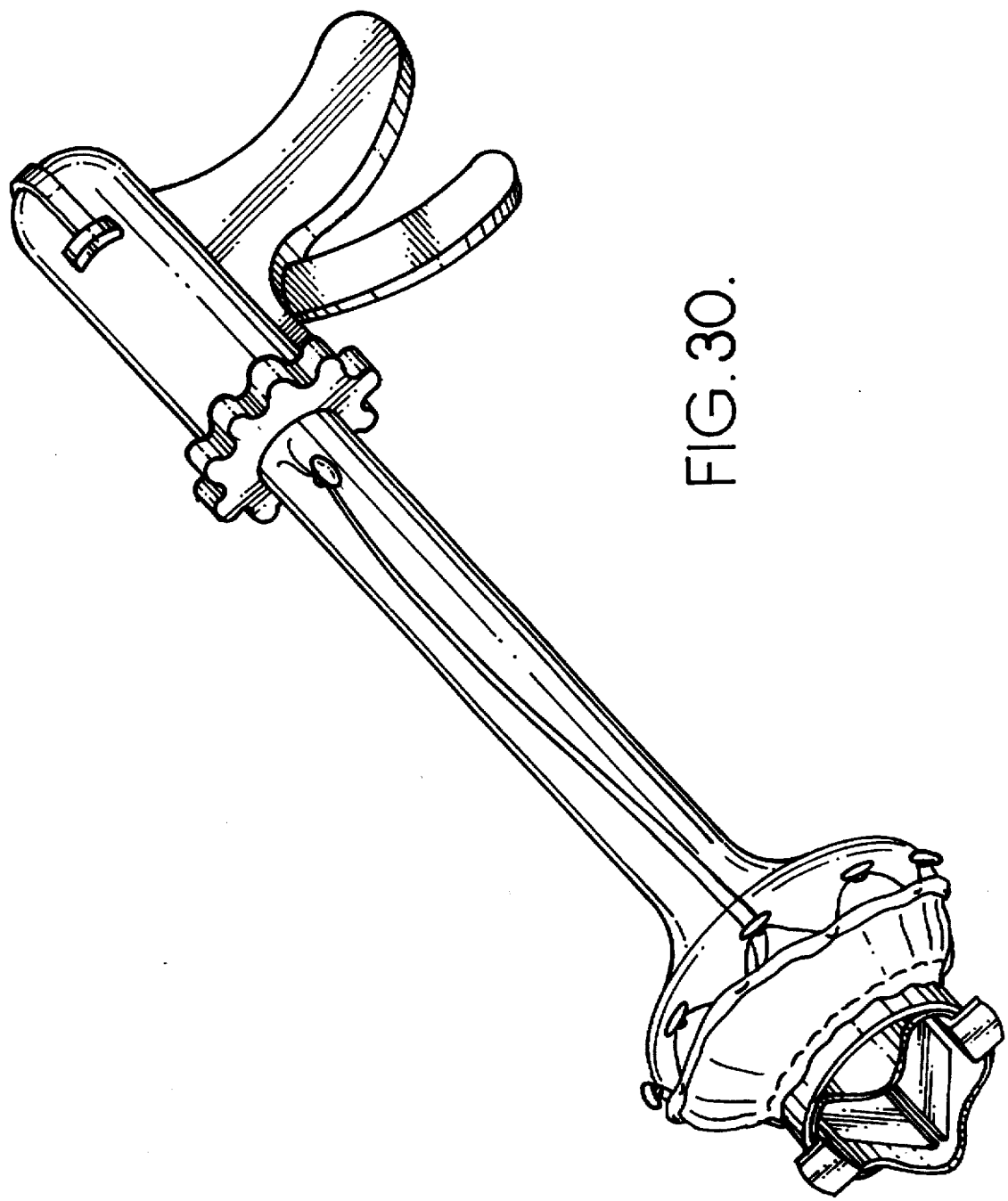
FIG. 30 is an assembled view of the FIG. 28 tool.

As above discussed, the central shaft experiences a counter-rotation as the driving head is indexed so the cuff is held stationary with respect to the patient's tissue while the fastener head is being indexed to the various positions. A further alternative form of the tool is shown in FIGS. 28 and 30 at T' keeps the handle and the shaft stationary while the fastener delivery system rotates. A rotating fastener assembly 300 is shown in FIG. 29. Tool T' includes mechanisms necessary to deliver the fasteners and which are located inside the central shaft. A lever 400 actuates the mechanisms from within the housing. A central bore 402 is defined in the housing of the tool and has a central retaining stalk 404 therein on which the distal end 406 of the sewing cuff 19 is located. The heart valve base 20 can also be attached to the stalk end 406 if the base is attached to the cuff prior to setting the fasteners. The cuff is temporarily attached to the outer housing 408 and the stalk 404 which remain stationary during the fastening procedure and the fasteners are delivered in a coaxial method from between two stationary parts. Within the central fastener delivery assembly 300 are components similar to the above-described cam mechanisms needed to drive staples through the cuff and form them in the annular tissue from within. As above described, driver mechanisms 300 are diametrically opposed and offset with respect to each other to create the appropriate overlapping staple spacing discussed above. Staggering allows two distinct rows of staples to be formed as above discussed whereby total coverage of the cuff is effected. Toggle links 303 are used and are connected to longitudinal drive rods 305. Drive rods translate handle-generated forces into fastener delivery forces at the toggle links 303. Each toggle link 303 is connected to a staple driver 307 and substitute. The fastener assembly 300 is rotated a plurality of times to form the two rows of staples. Flexible shafts (not shown) can also be used to permit the driving angle of the fasteners to be altered as necessary. Flexible shafts can also be used to permit the tool to operate to drive fasteners from the superior to inferior side of a suture cuff which might be pre-attached to the valve body. Such a cuff could be temporarily tied to the stationary housing. Upon insertion of the valve, cuff and instrument would be inserted into the annulus. Each fastener would form from the superior side of the cuff penetrating the cuff and annular tissue below. Again, as above discussed, one or more complete rows of fasteners would be formed holding the cuff to the annular tissue.

A balloon B (see FIG. 24) is used as a means for anchoring and positioning. Balloon B can either be attached to the fastener driving device or be separate. The balloon can be inflated using a hand pump HB. The balloon is pulled up snugly under the annular tissue and the device is brought down to it. Then, the tool can be drawn up close to the balloon trapping the annular tissue and aligning the tool for forming fasteners.

Figure 25:
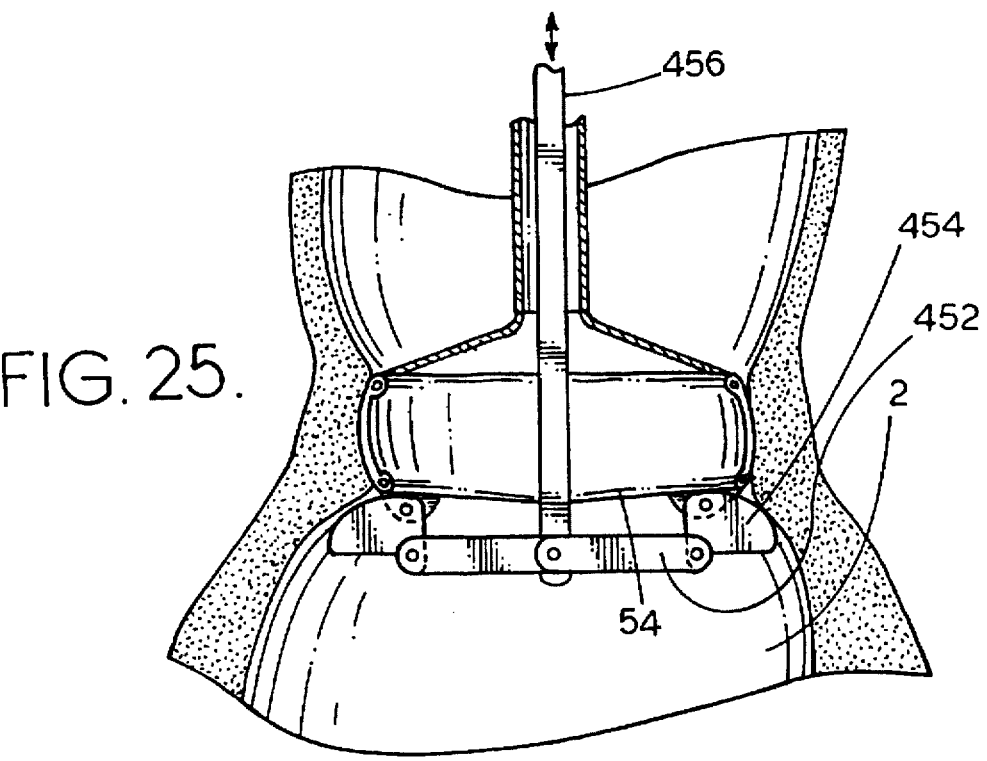

A second method (see FIG. 25) uses levers and links 452 to deploy small flanges 454 around the lower periphery of the lower housing 54. By actuating the central rod 456, the connecting links pivot the flanges outwardly providing a lip in which the surgeon can draw the tool upward locating the staples in the proper location in relation to the annular tissue.

Figure 26:
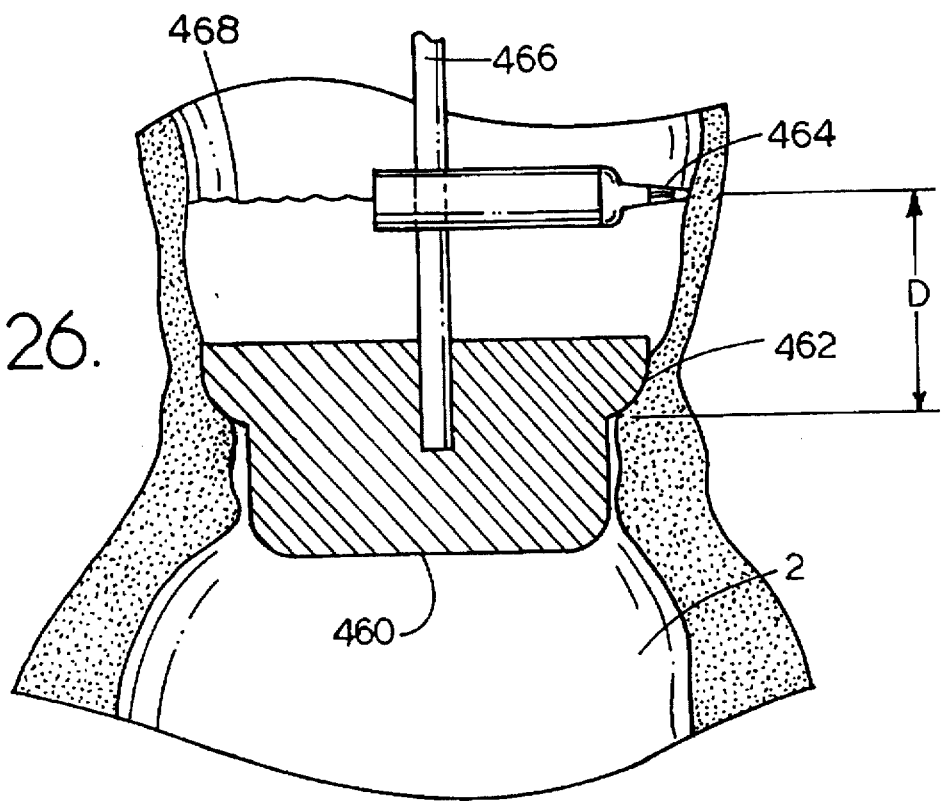

A third method (see FIG. 26) uses a clear cylindrical sizing tool 460 which uses a lip 462 or flange that sits on top of the annular tissue. It also has a special tissue marker 464 mounted on the central shaft 466. The surgeon will visualize the contact of the annular tissue from above. The contact with the surface will create a wetted dark circle when properly seated on the annulus. At that point, the surgeon rotates the central shaft 466 which creates a line 468 inside the aorta. This line would have a distance D (FIG. 26) that would correspond to a pointer or landmark to be used to line up the device in the correct position.

Figure 27:
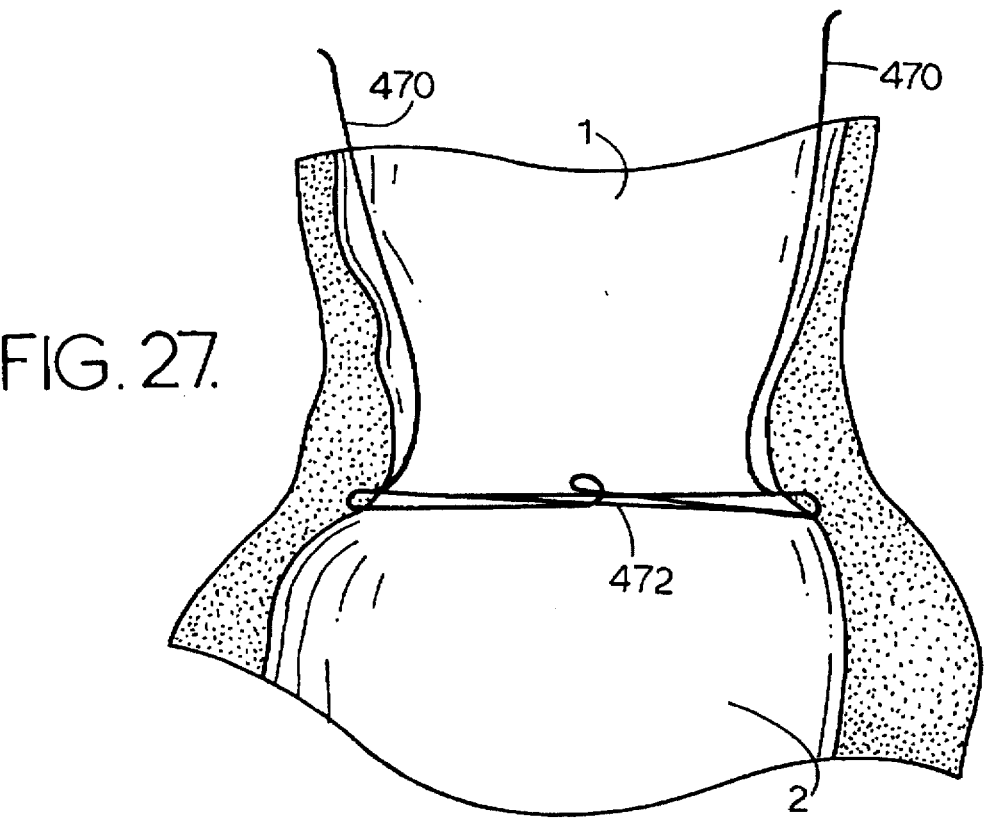

Still another way (see FIG. 27) to gauge the placement of the device is to drive sutures 470 below the annulus to create a safety net 472 that will not allow the device to plunge too deeply into the left ventricle 2. The device is then inserted until the resistance of the suture net is felt by the surgeon. Once the cuff is fastened into the annulus, the sutures can be cut and removed from the annulus.

In the interest of completeness, an open thoracotomy surgical technique for aortic valve replacement will now be discussed (see FIGS. 19A and 19B). A surgical incision 200 is made in one of several locations: a midline sternotomy incision; or a small anterior right or left thoracotomy; or a mini-thoracotomy (with or without rib removal); or a posterior thoracotomy; or a suprasternal or supraclavicular approach; or through port sites (mini incisions) over the chest wall. The pericardium is then opened. The patient is then placed on cardiopulmonary bypass using: right atrial cannulation; or femoral vein-femoral artery; or femoral artery-left atrium; or aortic-left atrial cannulation. The aorta is dissected for access and clamping. The aorta is then crossclamped and cardioplegia is delivered through: the aorta, coronary ostial cannulation or retrograde through the coronary sinus to arrest the heart. A venting device is then inserted.

The aortotomy is then performed. The aortic valve is excised and the annulus, aorta and/or the anterior leaflet of the mitral valve, and septum are debrided as necessary and appropriate. A device or devices that determine the relative size of the annulus and that identify the position of the staples and stapling device, is inserted into the annulus. When appropriate, sizing and positioning are determined, a biologic marker is circumferentially traced over the top (most superior) edge of the position/sizing device, to guide the proper placement of the stapling device. A balloon or levers can also be used.

The position/sizing device is then removed and the stapling device is inserted and positioned in the annulus with the cuff of the valve. The stapling device is positioned with the cuff lying in the annulus and the position confirmed by its proximity to the circle previously marked. The stapling device is enabled to dilate the annulus with the valve cuff in situ.

The stapling device is then actuated. The appropriate size of mechanical valve skeleton is then inserted into the cuff. The valve and the perivalvular area are tested for proper size and the device is removed. Once the proper size is established, the skeleton is removed and the valve base is inserted. The drawstrings of the cuff are then tightened and tied securely to trap the mechanical valve to the cuff. This assures that the largest desirable valve base will be used. The aortotomy is closed with traditional sutures or with vascular staples. The heart is de-aired and the crossclamp removed. The patient is then removed from cardiopulmonary bypass and the wounds are closed.

An alternative technique with the valve pre-attached includes the following steps. All methods up to and including placement of the biologic marker circumferentially over the top edge of the position/sizing device are repeated. Then, the position/sizing device is removed. The stapling device already pre-attached to a mechanical or tissue valve of appropriate size is lowered into the annulus. The stapling device and the cuff of the valve are positioned in the appropriate place in the annulus using the biological marker circle previously marked on the aortic wall for verification. The cuff-valve border at this time would be found in a slight subannular position.

The stapling device is then actuated. The drawstrings in the cuff of the valve are drawn and tied securely to bring the valve in proximity to the annulus. The remainder of the steps are the same as above described.

Yet a third technique for aortic valve replacement is through the left atrium. This technique includes the following steps: surgical incisions are made in the manner discussed above; the pericardium is opened; the patient may or may not then be placed on cardiopulmonary bypass. The technique then includes the use of imaging devices (both intra and extra-vascular) being used to guide the conduct of the operation. Purse string sutures (access) are then placed on the left atrium and aorta. Flexible imaging devices and instrumentation is then inserted through the left atrium (and aorta). The devices are lead through the mitral valve and into the left ventricle. The aortic valve is then imaged both through the aorta and left ventricle and is excised.

The valve stapling device is then inserted through the left atrium and positioned in the aortic annulus. The stapling device is then activated and positioning assessed both through the left ventricle and aorta using the imaging devices. The stapling device is then removed, and all cannulation sites secured. The heart is then deaired and taken off cardiopulmonary bypass if appropriate. The wounds are then closed.

Figure 19B:
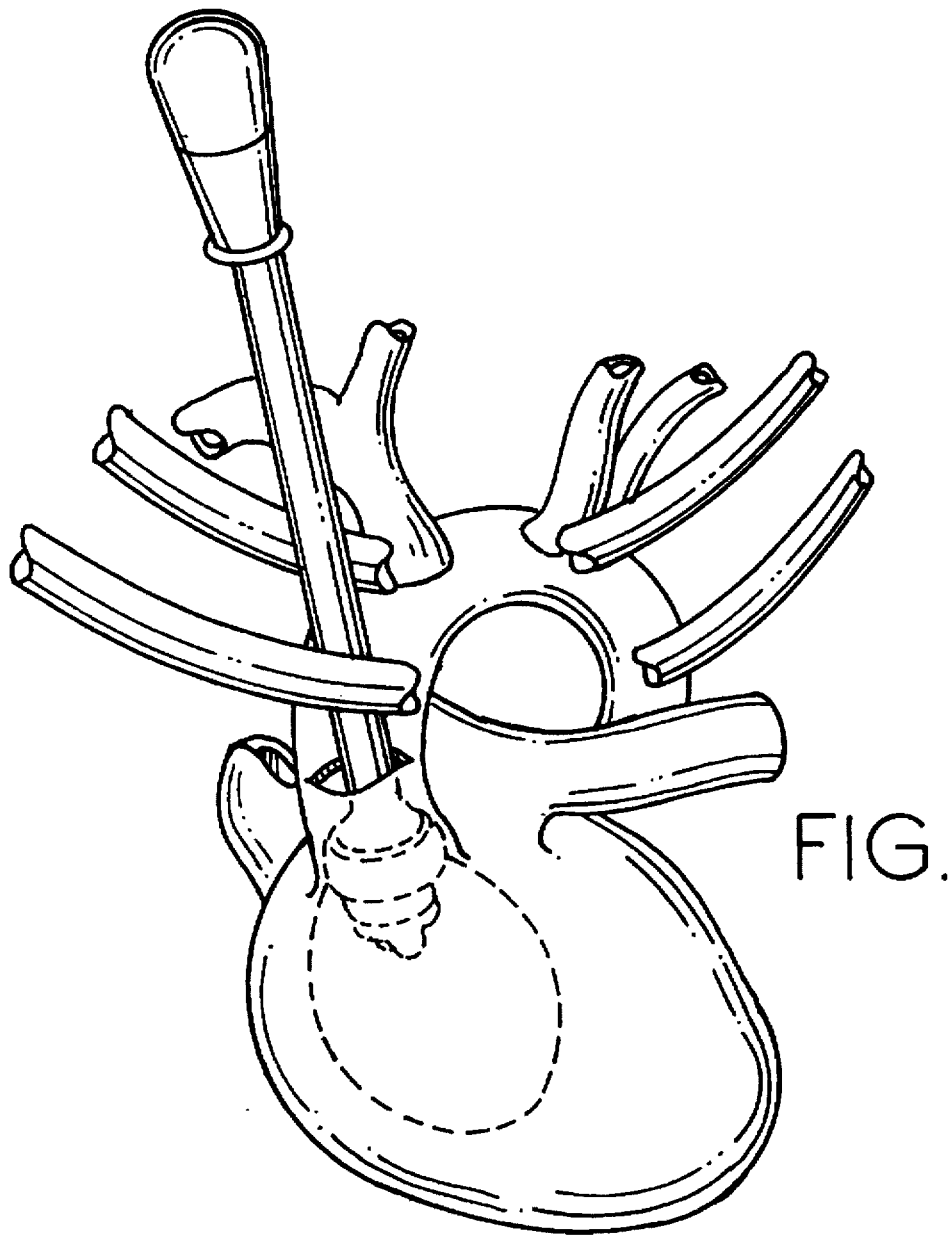
FIG. 19B illustrates the tool inserted into an aorta.

A minimally invasive surgical procedure is illustrated in FIGS. 19A and 19B. A torso with an overlapping rib cage is shown. Access to the aorta is gained through an incision 200 in the superstenal notch passing below the manubrium or via a mini-thoracotomy is performed in the area of the first and second ribs enabling visualization of the aorta. A small incision 202 across the aorta above the annulus is made. The fastener driving tool T with a cuff attached is inserted through the incision after the faulty valve has been excised. The knob 36 is rotated while holding the handle 35 to deploy the fasteners through the cuff 19 and into the aortic annulus. Once the fasteners have been driven into the aortic annulus, the stay sutures 32 are removed from cleat 34 allowing the head of the instrument to be removed from the patient's body. Activating means 27' and 28' are also removed from the cleats 27a" and 28a". The heart valve body is then placed into a holding fixture, such as the above-discussed fixture, and inserted into the aortic annulus in the same manner as the tool T. The valve body is then docked into the sewing cuff 19. The indicating means provides tactile feedback for the surgeon to determine when the heart valve body 20 is properly seated. Temporary stays 32 prevent the heart valve base from descending too far and aligning the drawstrings with the recesses in the valve body. Once the lower drawstring has been cinched up, the upper drawstring is pulled tight. The zig-zag drawstring 26 will then pull the cords into the top recess 28T.

Figure 23:
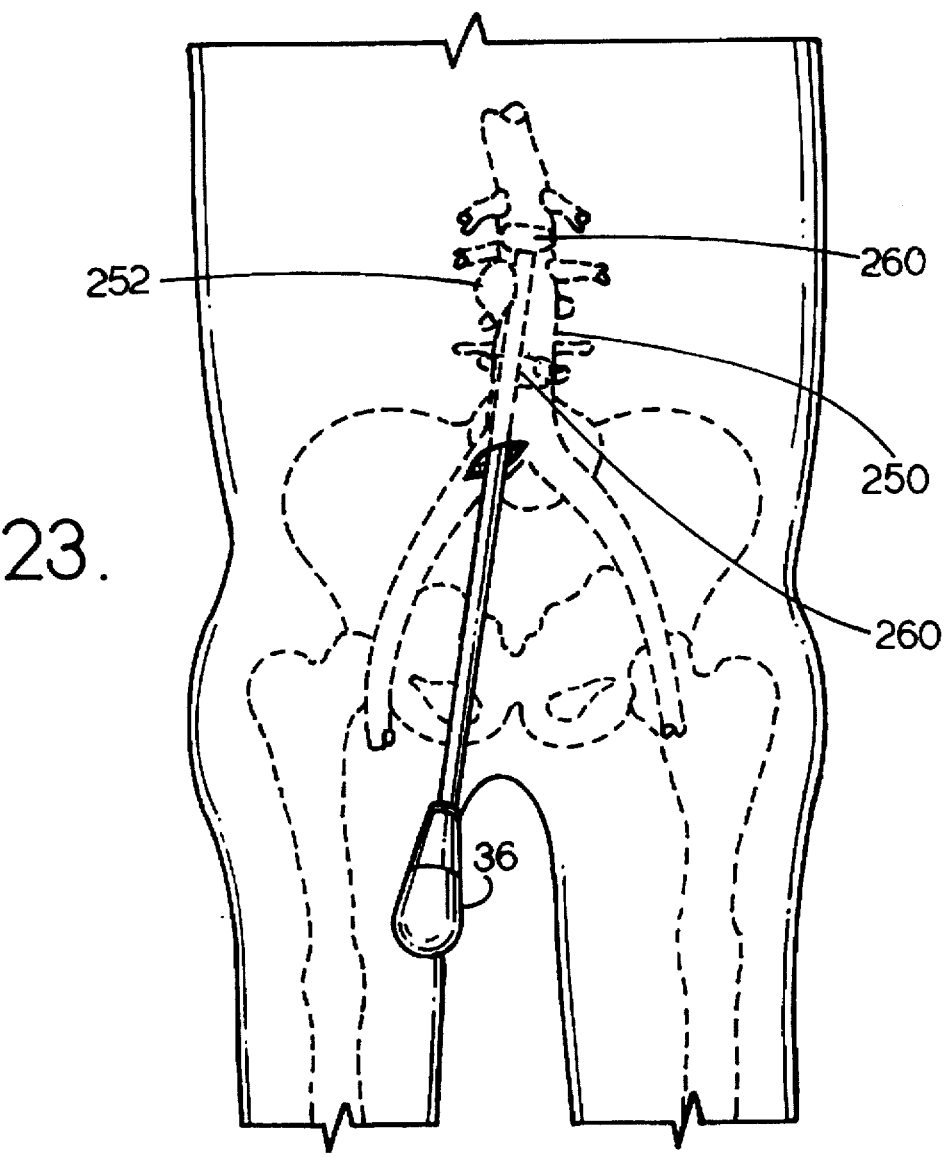
FIG. 23 shows use of the tool shown in FIG. 21 to repair an abdominal aortic aneurysm.

As shown in FIGS. 21–23, the system can be used to repair an abdominal aortic aneurysm (AAA) which may occur because of a thinning of the aortic wall 250. The wall balloons out under positive pressure and forms a pouch 252. These aneurysms present life-threatening consequences for the patient should they rupture. If detected prior to rupture, a graft 254 can be placed on the aorta, in an abdominal graft procedure to provide support to the weakened area of the wall. The graft is usually made from a tube of Dacron fabric and is most often sutured in place.

However, using the teaching of the present invention, the graft can be stapled in place. As shown in FIGS. 21 and 22, the dilating fastener deployment feature of the present invention permits fasteners to be formed from the inside toward the outside of the aortic wall. As shown in FIG. 21, the fastener deployment device has two driving heads 260 to deliver fasteners through the graft on either side of the aneurysm 252. At each end of the graft in FIG. 22 there is a metal ring 266, analogous to the garter spring discussed above. These rings help to keep the graft open once it is fastened to the aortic wall. FIG. 23 illustrates access to the aorta gained through entry in the femoral artery in the pelvic region. The fastener deployment device, with graft attached, would be inserted into the femoral artery and fed up to the area of the aneurysm. The distal head 260 is positioned beyond the aneurysm and the proximal head 260 is positioned to center the aneurysm underneath the graft. Fasteners are formed in a manner similar to that discussed above, completing the installation of the graft. Stay sutures may be used to hold the graft in place during fastening.

Figure 24:
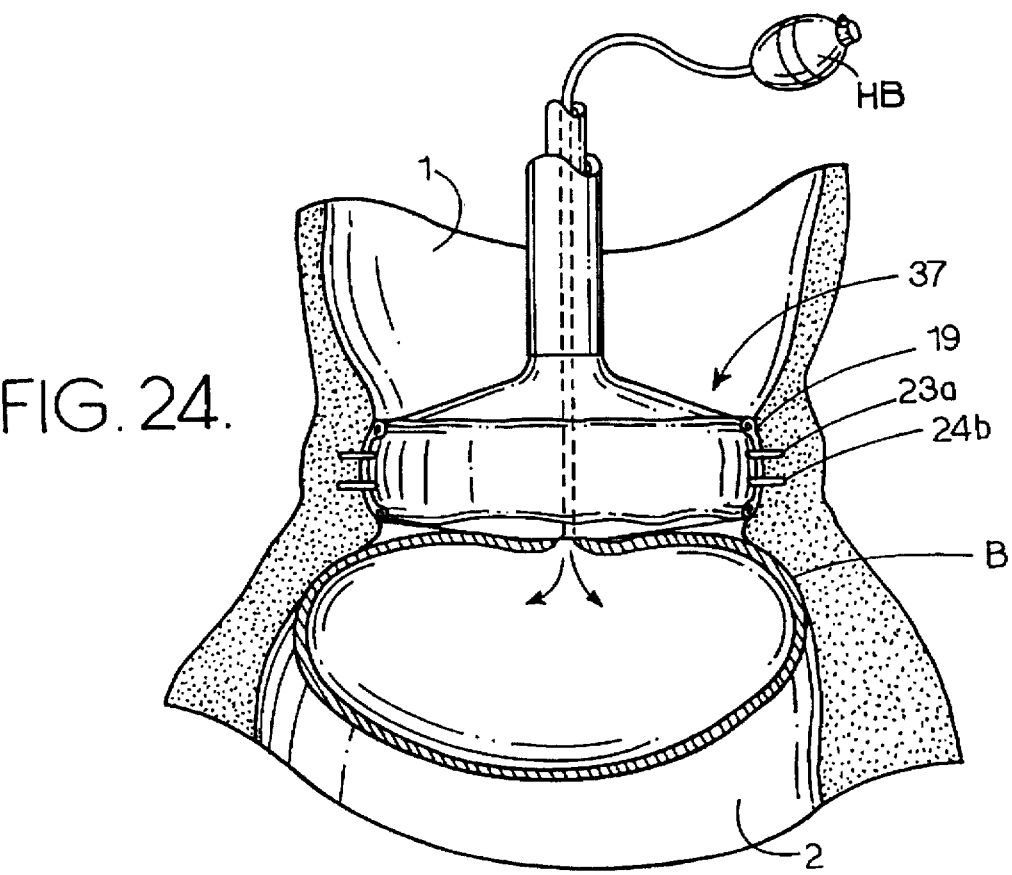
FIGS. 24–27 show steps in placing a prosthesis.

During the installation of the fastener driving device, it will be important to obtain the correct anatomical positioning of the cuff to be fastened to the annular tissue. FIGS. 24–27 depict four different ways to accomplish this task. FIG. 24 shows the use of an inflatable balloon B in the left ventricle 2.

It is understood that while certain forms of the present invention have been illustrated and described herein, it is not to be limited to the specific forms or arrangements of parts described and shown with the elements being shown, such as the tool T, being the best mode, but not the only mode.

We claim:

1. A tool for placing a prosthesis valve in a patient in a minimally invasive manner comprising:
   A) a housing;
   B) an operating handle attached to said housing and which extends out of the patient's body during use;
   C) a fastener deployment knob on said handle;
   D) an operating shaft having a first end located in said housing and a second end connected to said fastener deployment knob and rotatably attached to said housing;
   E) cam means located in said housing and connected to said operating shaft to be rotated therewith;
   F) a driver head plate fixed to said housing;
   G) a fastener delivery mechanism mounted on said driver head plate in position to be actuated by said cam means, said fastener delivery mechanism including means for storing a plurality of fasteners in said housing;
   H) means for releasably mounting a sewing cuff on said housing; and
   I) means on said driver head plate for forcing the sewing cuff against a patient's tissue as said fastener delivery mechanism is operated.

2. The tool defined in claim 1 further including means connected to said cam means for holding said sewing cuff stationary relative to said housing whereby said housing can be rotated while said sewing cuff remains stationary with respect to said housing.

3. The tool defined in claim 1 further including drawstrings on said sewing cuff and further including means on said operating handle and located outside the patient's body for releasably attaching said sewing cuff drawstrings thereto for operating said drawstrings from outside the patient's body for fixedly attaching the sewing cuff to a prosthesis valve body located inside the patient's body.

4. The tool defined in claim 1 wherein said fastener delivery mechanism includes an anvil mounted on said driver head plate and connected to said cam means for actuation thereby, a fastener driver mounted on said driver head plate and connected to said cam means for actuation thereby, a fastener spring mounted on said housing, and a lifter spring mounted on said head plate.

5. The tool defined in claim 1 wherein said means for forcing said sewing cuff against the patient's aorta includes a dilation spring mounted on said driver head.

6. The tool defined in claim 2 wherein said means for holding said sewing cuff stationary relative to said housing includes a cuff index ring rotatably mounted on said housing and means for coupling said cuff index ring to said cam means.

7. The tool defined in claim 1 further including means on said cam means for preventing retrograde movement of said cam means.

8. The tool defined in claim 1 further including a second fastener delivery mechanism mounted on said driver plate at a location spaced from said first-mentioned fastener delivery mechanism.

9. The tool defined in claim 8 further including a second cam means in said housing and spaced from said first-mentioned cam means.

10. The tool defined in claim 9 wherein said fastener delivery mechanism includes a plurality of fastening positions which are spaced apart form each other in two directions.

11. The tool defined in claim 10 wherein said fastener positions are located to place two spaced apart rows of fasteners in said cuff.

12. The tool defined in claim 11 wherein at least two of said fastener positions are 180° apart from each other on said fastener delivery means.

13. The tool defined in claim 11 wherein said fastener positions are located so fasteners in one row are staggered with respect to corresponding fasteners in the other row of fasteners.

14. The tool defined in claim 1 wherein said means for forcing said sewing cuff against the patient's tissue includes means for maintaining constant pressure on said sewing cuff during operation of said fastener delivery mechanism.

15. The tool defined in claim 1 further including means on said handle for displaying size of the patient's aorta.

16. The tool defined in claim 1 further including means for connecting the cuff to the tissue in a continuous manner about the entire periphery of the cuff.

17. A tool for placing a prosthesis in a patient in a minimally invasive manner comprising:
A) a housing;
B) an operating shaft associated with said housing and extending out of a patient's body during use;
C) an operating handle mounted on a proximal end of said operating shaft;
D) a fastener handing means associated with said housing for delivering and forming a fastener to attach a sewing cuff of a prosthesis valve to a patient and including
(1) means for accommodating fasteners,
(2) an anvil located in position to engage and close a fastener when that fastener has been forced against said anvil, and
(3) a driver element in position to engage a fastener and force that fastener against said anvil for closing the fastener;
E) means on another end of said operating shaft for operating said fastener handling means; and
F) means for releasably mounting the sewing cuff on said housing during operation of said fastener handling means.

18. A tool for placing a prosthesis in a patient in a minimally invasive manner comprising:
A) a housing;
B) an operating handle attached to said housing and which extends out of a patient's body during use;
C) a fastener deployment knob on said handle;
D) an operating shaft having a first end located in said housing and a second end connected to said fastener deployment knob;
E) cam means located in said housing and connected to said operating shaft;
F) a driver head plate on said housing;
G) a fastener handling mechanism mounted on said driver head plate in position to be actuated by said cam means, said fastener handling mechanism including means for storing a plurality of fasteners in said housing; and
H) means for releasably mounting a sewing cuff on said housing during operation of said fastener handling mechanism.

19. The tool defined in claim 17 further including a plurality of means for operating said fastener handling means.

20. The tool defined in claim 19 further including a plurality of anvils.

21. The tool defined in claim 20 further including a plurality of driver elements.

22. The tool defined in claim 20 wherein said plurality of anvils are in staggered relationship with each other.

23. The tool defined in claim 17 further including means for controlling the position of a fastener on said means for accommodating fasteners.

24. The tool defined in claim 17 wherein said fastener is W-shaped.

25. The tool defined in claim 17 further including means for ejecting a fastener from said fastener handling means.

26. The tool defined in claim 17 further including means for storing a plurality of fasteners in said fastener handling means.

27. The tool defined in claim 26 wherein said fasteners are located in a plurality of rows.

28. The tool defined in claim 17 wherein said means on another end of said operating shaft for operating said fastener handling means includes a cam.

29. The tool defined in claim 17 wherein said fastener handling means further includes a linkage means for linking said means on another end of said operating shaft for operating said fastener handling means and said operating knob.

30. The tool defined in claim 17 wherein said operating shaft is flexible.

31. The tool defined in claim 17 further including an indexing means for controlling location of said means on another end of said operating shaft for operating said fastener handling means.

32. The tool defined in claim 28 further including a plurality of cams.

33. The tool defined in claim 27 wherein the fasteners in one row are staggered with respect to the fasteners in an adjacent row.

34. The tool defined in claim 17 further including means for releasably mounting a prosthetic valve body on the tool.

35. The tool defined in claim 17 wherein said means on said housing for forcing the sewing cuff against the patient's tissue as said fastener handling means is operated includes a biasing element.

36. The tool defined in claim 17 wherein said anvil is located to close a fastener after that fastener has penetrated the sewing cuff and the patient's tissue.

37. The tool defined in claim 27 wherein the fasteners of said plurality of fasteners are angularly spaced apart from each other.

38. The tool defined in claim 17 further including means for rotating said handling means about an axis extending through said operating shaft.

39. The tool defined in claim 17 further including means for rotating said means for accommodating fasteners about an axis extending through said operating shaft.

40. The tool defined in claim 17 further including means for forcing the sewing cuff against the patient's tissue as said fastener handling means is operated.

41. The tool defined in claim 17 further including means for rotating said fastener handling means about an axis through said housing.

42. The tool defined in claim 17 further including means for rotating said fastener handling means about an axis through said sewing cuff.

43. The tool defined in claim 18 further including means for forcing the sewing cuff against the patient's tissue as said fastener handling mechanism is operated.

44. The tool defined in claim 24 wherein said fasteners includes two legs and a crown connecting said legs together, with said legs being linear and said crown being arcuate.

45. The tool defined in claim 44 further including means for supporting said legs and wherein said crown is located between said anvil and said driver element so that said forcing said crown against said anvil causes said legs to rotate toward each other.

* * * * *